United States Patent
Duncan et al.

(10) Patent No.: US 10,758,616 B2
(45) Date of Patent: *Sep. 1, 2020

(54) PRE-MIXED, READY-TO-USE PHARMACEUTICAL COMPOSITIONS

(71) Applicant: EKR Therapeutics, Inc., Cary, NC (US)

(72) Inventors: Michelle Renee Duncan, Glenview, IL (US); Supriya Gupta, Waverly, IA (US); David Hartley Haas, Fremont, CA (US); Norma V. Nenonene, Skokie, IL (US); Camellia Zamiri, Fremont, CA (US)

(73) Assignee: EKR Therapeutics, Inc., Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/010,898

(22) Filed: Jun. 18, 2018

(65) Prior Publication Data

US 2019/0015511 A1      Jan. 17, 2019

Related U.S. Application Data

(60) Continuation of application No. 15/159,495, filed on May 19, 2016, now abandoned, which is a continuation of application No. 12/977,965, filed on Dec. 23, 2010, now Pat. No. 9,370,586, which is a continuation of application No. 12/645,169, filed on Dec. 22, 2009, now Pat. No. 9,364,564, which is a continuation of application No. 12/407,557, filed on Mar. 19, 2009, now Pat. No. 7,659,291, which is a division of application No. 11/788,076, filed on Apr. 18, 2007, now Pat. No. 7,612,102.

(60) Provisional application No. 60/793,074, filed on Apr. 18, 2006.

(51) Int. Cl.

| | |
|---|---|
| *A61K 31/44* | (2006.01) |
| *A61K 47/02* | (2006.01) |
| *A61K 47/69* | (2017.01) |
| *C08B 37/16* | (2006.01) |
| *C08L 5/16* | (2006.01) |
| *B82Y 5/00* | (2011.01) |
| *A61K 9/00* | (2006.01) |
| *A61K 31/4422* | (2006.01) |
| *A61K 31/455* | (2006.01) |
| *A61K 47/10* | (2017.01) |
| *A61K 47/12* | (2006.01) |
| *A61K 47/14* | (2017.01) |
| *A61K 47/40* | (2006.01) |
| *A61K 47/26* | (2006.01) |

(52) U.S. Cl.
CPC ............ *A61K 47/02* (2013.01); *A61K 9/0019* (2013.01); *A61K 31/4422* (2013.01); *A61K 31/455* (2013.01); *A61K 47/10* (2013.01); *A61K 47/12* (2013.01); *A61K 47/14* (2013.01); *A61K 47/26* (2013.01); *A61K 47/40* (2013.01); *A61K 47/6951* (2017.08); *B82Y 5/00* (2013.01); *C08B 37/0015* (2013.01); *C08L 5/16* (2013.01)

(58) Field of Classification Search
CPC ...................................................... A61K 47/02
See application file for complete search history.

(56) References Cited

U.S. PATENT DOCUMENTS

| | | | |
|---|---|---|---|
| 3,985,758 A | 10/1976 | Murakami | |
| 4,711,902 A | 12/1987 | Serno | |
| 4,880,823 A | 11/1989 | Ogawa | |
| 4,940,556 A | 7/1990 | MacFarlane | |
| 5,079,237 A | 1/1992 | Husu et al. | |
| 5,164,405 A | 11/1992 | McFarlane | |
| 5,198,226 A | 3/1993 | MacFarlane | |
| RE34,618 E | 5/1994 | Ogawa | |
| 5,376,645 A | 12/1994 | Stella | |
| 5,519,012 A | 5/1996 | Fercej-Temeljotov | |
| 5,904,929 A | 5/1999 | Uekama | |
| 6,595,926 B1 | 7/2003 | Laragh | |
| 7,612,102 B2 | 11/2009 | Duncan et al. | |
| 7,659,290 B2 | 2/2010 | Duncan et al. | |
| 7,659,291 B2 | 2/2010 | Duncan et al. | |
| 8,455,524 B2 | 6/2013 | Duncan et al. | |
| 9,364,564 B2 * | 6/2016 | Duncan ............... | A61K 9/0019 |
| 9,370,586 B2 * | 6/2016 | Duncan ............... | A61K 9/0019 |
| 2002/0143050 A1 | 10/2002 | Doty | |
| 2002/0160942 A1 | 10/2002 | Larew et al. | |
| 2007/0112041 A1 | 5/2007 | Bhowmick | |
| 2007/0244166 A1 | 10/2007 | Gupta | |

(Continued)

FOREIGN PATENT DOCUMENTS

| | | |
|---|---|---|
| EP | 0143305 A1 | 6/1985 |
| EP | 0149475 B1 | 7/1985 |
| EP | 0162705 B1 | 11/1985 |

(Continued)

OTHER PUBLICATIONS

Paragraph IV Certification for NDA No. 22276 dated Jun. 10, 2013.

(Continued)

*Primary Examiner* — Dennis J Parad
*Assistant Examiner* — Lyndsey M Beckhardt
(74) *Attorney, Agent, or Firm* — Lowenstein Sandler LLP

(57) ABSTRACT

Provided herein are ready-to-use premixed pharmaceutical compositions of nicardipine or a pharmaceutically acceptable salt and methods for use in treating cardiovascular and cerebrovascular conditions.

10 Claims, 5 Drawing Sheets

(56) References Cited

U.S. PATENT DOCUMENTS

2007/0249689 A1    10/2007    Duncan

FOREIGN PATENT DOCUMENTS

Figure 1:
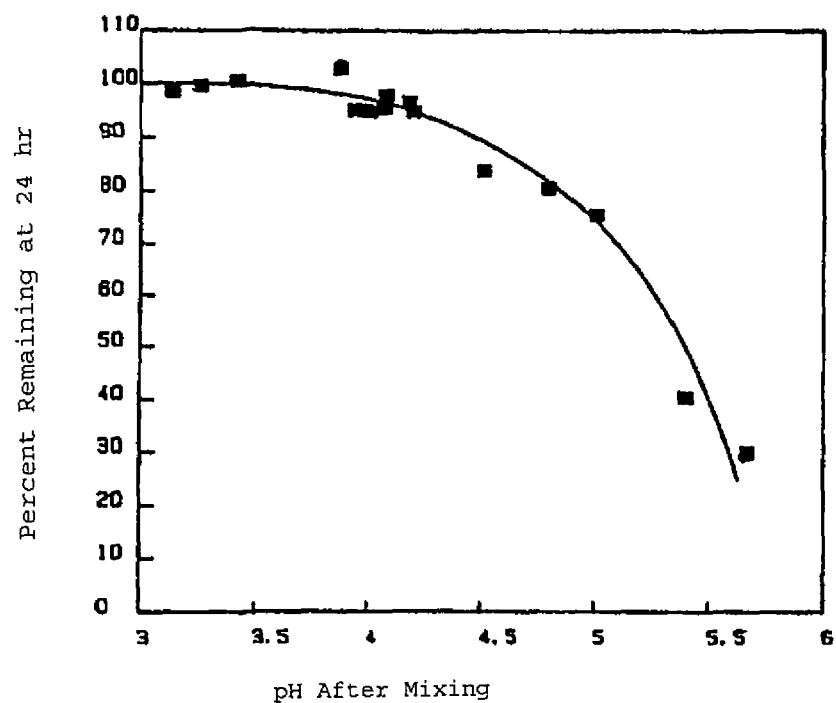

| | | |
|---|---|---|
| GB | 2228412 A | 8/1990 |
| JP | 2002-177364 | 6/2002 |
| WO | 2001/07086 | 2/2001 |

OTHER PUBLICATIONS

Martens, et al., "Sorption of Various Drugs in Polyvinyl Chloride, Glass and Polyethylene-Lined Infusion Containers," Am. J. Hospital Pharmacy 1990, 47:369-373.
Griffin and D'Arcy, A Manual of Adverse Drug Interactions, Elsevier 1997, Chapter 13, pp. 549-561.
Van der Linden, et al., "Ready-to-Use Injection Preparations Versus Conventional Reconstituted Admixtures", Pharmacoeconomics 2002, 20(8): 529-536.
Schmitt, et al., "Ready to Use Injectable Paracetamol: Easier, Safter, Lowering Workload and Costs," EJHP 2003, 6:96-102.
Approval Letter for NDA 17-734/S-013 (Jul. 31, 2008).
Case IPR2015-00005, Decision, Re: U.S. Pat. No. 8,455,524, 15 pages, Apr. 24, 2015.
Case IPR2015-00006, Decision, Re: U.S. Pat. No. 7,612,102, 20 pages, Apr. 24, 2015.
Case IPR2015-00007, Decision, Re: U.S. Pat. No. 7,659,290, 14 pages, Apr. 24, 2015.
Case IPR2015-00008, Decision, Re: U.S. Pat. No. 7,659,291, 11 pages, Apr. 24, 2015.
*Cornerstone Therapeutics Inc., Cornerstone Biopharma, Inc., and EKR Therapeutics, LLC v. Sandoz Inc.*, Complaint, Case 1:13-cv-05723-NLH-AMD, Filed Sep. 25, 2013, 105 pages.
*Chiesi USA, Inc., Cornerstone Biopharma, Inc., and EKR Therapeutics, LLC v. Sandoz Inc., Sandoz AG, and ACS Dobfar Info SA*, Joint Claim Construction and Prehearing Statement, Case 1:13-cv-05723-NLH-AMD, Filed Sep. 8, 2014, 70 pages.
*Sandoz Inc. v. EKR Therapeutics, LLC* (f/k/a EKR Therapeutics, Inc.), Case 1:13-cv-05723-NLH-AMD, Declaration of Alpaslan Yaman, Ph.D., Re: U.S. Pat. No. 7,612,102, Oct. 1, 2014, 121 pages.
*Sandoz Inc. v. EKR Therapeutics, LLC* (f/k/a EKR Therapeutics, Inc.), Case 1:13-cv-05723-NLH-AMD, Declaration of Alpaslan Yaman, Ph.D., Re: U.S. Pat. No. 7,659,290, Oct. 1, 2014, 121 pages.
*Sandoz Inc. v. EKR Therapeutics, LLC* (f/k/a EKR Therapeutics, Inc.), Case 1:13-cv-05723-NLH-AMD, Declaration of Alpaslan Yaman, Ph.D., Re: U.S. Pat. No. 7,659,291, Oct. 1, 2014, 134 pages.
*Sandoz Inc. v. EKR Therapeutics, LLC* (f/k/a EKR Therapeutics, Inc.), Case 1:13-cv-05723-NLH-AMD, Declaration of Alpaslan Yaman, Ph.D., Re: U.S. Pat. No. 8,455,524, 127 pages, Oct. 1, 2014.
Merck Research Laboratories, "PEPCID (Famotidine) Injection Premixed," Mar. 14, 2001, 11 pages.
Yamanouchi Pharmaceutical Co., Ltd. "Perdipine," Revised in Sep. 2001 (6th Edition), 9 pages, with English translation.
Declaration by Dr. Harry G. Brittain, 71 pages, Jul. 2, 2009.
Zantac (ranitidine hydrochloride) Injection Premixed, Product Information, Mar. 7, 2000, 2 pages.
2004 WL 2459623 Physicians' Desk Reference, Thomson PDR, Montvale N.J., Cardene® I.V. (Nicardipine Hydrochloride) Rx Only, 2004, 15 pages.
USPTO, Notice of Allowability for U.S. Appl. No. 12/407,557, 9 pages, dated Nov. 3, 2009.
USPTO, Notice of Allowability for U.S. Appl. No. 12/407,551, 4 pages, dated Nov. 3, 2009.
USPTO, Office Action for U.S. Appl. No. 11/788,076, dated Apr. 10, 2009, 17 pages.
USPTO, Amendment and Interview Summary for U.S. Appl. No. 11/788,076, dated Jul. 6, 2009, 16 pages.
USPTO, Notice of Allowability for U.S. Appl. No. 11/788,076, 4 pages, dated Sep. 8, 2009.
USPTO, Amendment and Interview Summary for U.S. Appl. No. 12/971,084, 10 pages, dated Feb. 28, 2013.
USPTO, Notice of Allowability for U.S. Appl. No. 12/971,084, 6 pages, dated Apr. 4, 2013.
*Sandoz Inc. v. EKR Therapeutics, Inc.*, Petition for Inter Partes Review of U.S. Pat. No. 7,612,102, Oct. 1, 2014, 58 pages.
*Sandoz Inc. v. EKR Therapeutics, Inc.*, Petition for Inter Partes Review of U.S. Pat. No. 7,659,290, Oct. 1, 2014, 65 pages.
*Sandoz Inc. v. EKR Therapeutics, Inc.*, Petition for Inter Partes Review of U.S. Pat. No. 7,659,291, Oct. 1, 2014, 63 pages.
*Sandoz Inc. v. EKR Therapeutics, Inc.*, Petition for Inter Partes Review of U.S. Pat. No. 8,455,524, Oct. 1, 2014, 65 pages.
Kawano, K., et al., "The Effect of the Drip Condition (Container Materials, Concentration, Drip Rate) on the Sorption of Nicardipine Hydrochloride from Injection to the Intravenous Infusion Set", Jpn. J. Hosp. Pharm., 18(5), 491-495 (1992) with English translation.
Kawano, K., et al., "The Sorption of Nicardipine Hydrochloride from the Solutions into the Administration Set", Jpn. J. Hosp. Pharm., 18(3), 182-186 (1992) with English translation.
Ameridose, LLC, Complaint File, Docket Nos. PHA20100107 and PHA20100108, Allegation of Complaint: manufacture and distribution of non-approved FDA products, Jun. 6, 2011, 46 pgs.
U.S. Appl. No. 11/598,746, filed Nov. 14, 2006, Submission of Priority Document, Indian App. No. India 1428/MUM/2005, 13 pgs.
Niebergall, P. J., "Ionic Solutions and Electrolytic Equilibria," Remington: The Science and Practice of Pharmacy, Ch. 17, 2000, pp. 227-245.
Reich, I. et al., "Tonicity, Osmoticity, Osmolality, and Osmolarity," Remington: The Science and Practice of Pharmacy, Ch. 18, 2000, pp. 246-262.
"Safety Assessment of Di(2-ethylhexyl)phthalate (DEHP) Released from PVC Medical Devices," Center for Devices and Radiological Health, U.S. Food and Drug Administration, Sep. 2001, 119 pgs.
Taormina, D., et al., "Stability and sorption of FK 506 in 5% dextrose injection and 0.9% sodium chloride injection in glass, polyvinyl chloride, and polyolefin containers," American Journal of Hospital Pharmacy, vol. 49, Jan. 1992, pp. 119-122.
Tchiakpe, L., et al., "Stedim 6 and Clearflex, two new multilayer materials for infusion containers. Comparative study fo their compatibility with five drugs versus glass flasks and polyvinyl chloride bags," Journal of Biomaterials Science, Polymer Edition, vol. 7, No. 3, 1995, pp. 199-206.
Trissel, L. A. and Pearson, S. D., "Storage of lorazepam in three injectable solutions in polyvinyl chloride and polyolefin bags," American Journal of Hospital Pharmacy, vol. 51, Feb. 1, 1994, pp. 368-372.
Turco, S. J., "Intravenous Admixtures," Remington: The Science and Practice of Pharmacy, Ch. 42, 2000, pp. 807-820.
"Viaflo Flexible Container", web.archive.org, www.baxterbiopharmasolutions.com, Jan. 25, 2005, 1 pg.
*EKR Therapeutics, Inc., v. Pharmedium Healthcare Corporation*, Complaint, Case 3:12-cv-00238-CAB-BLM, Jan. 30, 2012, 25 pgs.
Wagenknecht, D. M., et al., "Stability of nitroglycerin solutions in polyolefin and glass containers," American Journal of Hospital Pharmacy, vol. 41, Sep. 1984, pp. 1807-1811.
Degarmo, S. S. and Emerson, D. M., "Establishment Inspection Report," Ameridose L.L.C., Framingham, MA, Jul. 8, 2010, 6 pgs.
Degarmo, S. S. and Emerson, D. M., "Establishment Inspection Report," Ameridose L.L.C., Westborough, MA, Jul. 8-15, 2010, 8 pgs.
Waugh, W. N., et al., "Stability, compatibility, and plasticizer extraction of taxol (NSC-125973) injection diluted in infusion solutions and stored in various containers," American Journal of Hospital Pharmacy, vol. 48, Jul. 1991, pp. 1520-1524.
"Japanese Pharmacopoeia Nicardipine Hydrochloride Injection," Japan Standard Commodity Classification No. 872149, Sep. 2001, 8 pgs.
Ltr. to Dr. Shelby from Marcus Schabacker, MD, PhD, Corporate Vice President, B. Braun Medical Inc., Feb. 2, 2006, 1 pg.
"Lucile Packard NICU Makes Major Strides to Remove DEHP and Saves $200,000 by Switching to Custom-made DEHP-free IV Product," Health Care Without Harm, Jul. 17, 2003, 2 pgs.

(56) References Cited

OTHER PUBLICATIONS

Freudenheim, M., "Maker of IV System to Stop Using Plastic," The New York Times, Apr. 7, 1999, 2 pgs.
Raso, R., et al., "Making the Most of Data for Patient Safety," Patient Safety & Quality Healthcare Magazine, May/Jun. 2007, pp. 32-35.
Maurin, M. B., et al., "Mechanism of Diffusion of Monosubstituted Benzoic Acid through Ethylene-Vinyl Acetate Copolymers," Journal of Pharmaceutical Sciences, vol. 81, No. 1, Jan. 1992, pp. 79-84.
"Medical Devices Made With Polyvinylchloride (PVC) Using the Plasticizer di-(2-Ethylhexyl)phthalate (DEHP); Draft Guidance for Industry and FDA," U.S. Department of Health and Human Services Food and Drug Administration Center for Devices and Radiological Health, Sep. 6, 2002, 6 pgs.
Rich, D. S., "New JCAHO medication management standards for 2004," American Journal of Health-System Pharmacists, Inc., vol. 61, Jul. 1, 2004, pp. 1349-1358.
Turlapaty, P., et al., "Nicardipine, a New Intravenous Calcium Antagonist: A Review of Its Pharmacology, Pharmacokinetics, and Perioperative Applications," Journal of Cardiothoracic Anesthesia, vol. 3, No. 3, Jun. 1989, pp. 344-355.
"NTP-CERHR Expert Panel Report on DI(2-Ethylhexyl)Phthalate," National Toxicology Program, U.S. Department of Health and Human Services, Center for the Evaluation of Risks to Human Reproduction, Oct. 2000, 120 pgs.
"OSMITROL Injection (Mannitol Injection, USP) in AVIVA Plastic Container," Aug. 2005, 211 pgs.
"Pactiv Propyflex PVC-Free Bag Wins Medical Design Excellence Award 2000," Press Release, Jun. 7, 2000, 1 pg.
Hall, A. G., "Nurses: Taking Precautionary Action on Pediatric Environmental Exposure: DEHP," Pediatric Nursing, vol. 32, No. 1, Jan./Feb. 2006, pp. 91-93.
Broadhead, J., "Parenteral Dosage Forms," Pharmaceutical Preformulation and Formulation, Interpharm/CRC, Aug. 2001, pp. 331-354.
"Cardene I.V. (Nicardipine Hydrochloride) Rx Only," Physicians' Desk Reference, 2004, 11 pgs.
Wyeth-Ayerst Laboratories, "Cardene I.V." Physicians' Desk Reference, 48th Ed., 1994, pp. 2505-2508.
"Azactam (Aztreonam for Injection, USP) RX Only," Elan Pharmaceuticals, Physicians' Desk Reference, Thomas PDR, 2005, 16 pgs.
"Cefotan Cefotetan Disodium for Injection for Intravenous or Intramuscular Use," Astrazeneca Pharmaceuticals LP, Physicians' Desk Reference, Thomas PDR, 2005, 1 pg.
"Claforan Sterile (Cefotaxime for Injection, USP) and Injection (Cefotaxime Injection, USP) Rx Only Prescribing Information as of Jan. 2004," Aventis Pharmaceuticals Inc., Physicians' Desk Reference, Thomson PDR, 2005, 17 pgs.
"Fortaz (Ceftazidime for Injection)," Glaxosmithkline, Physicians' Desk Reference, Thomsom PDR, 2005, 14 pgs.
"Mefoxin Premixed Intravenous Solution (Cefoxitin Injection)," Merck & Co., Inc., Physicians' Desk Reference, Thomson PDR, 2005, 14 pgs.
"Pepcid Injection Premixed (Famotidine)," Merk & Co., Inc., Physicians' Desk Reference, Thomson PDR, 2005, 13 pgs.
"Recombinate Antihemophilic Factor (Recombinant)," Baxter Healthcare Corporation, Physicians' Desk Reference, Thomson PDR, 2005, 11 pgs.
"Rocephin (Ceftriaxone Sodium) for Injection," Roche Pharmaceuticals, Physicians' Desk Reference, Thomson PDR, 2005, 17 pgs.
"Timentin (Sterile Ticarcillin Disodium and Clavulanate Potassium) for Intravenous Administration," Glaxosmithkline, Pharmacy Bulk Package Not for Direction Infusion, Physicians' Desk Reference, Thomson PDR, 2005, 15 pgs.
"Timetin (Sterile Ticarcillin Disodium and Clavulanate Potassium) for Intravenous Administration Add-Vantage Antibiotic Vial," Glaxosmithkline, Physicians' Desk Reference, Thomson PDR, 2005, 16 pgs.
"Timentin (Sterile Ticarcillin Disodium and Clavulanate Potassium) for Intravenous Administration," Glaxosmithkline, Physicians' Desk Reference, Thomson PDR, 2005, 15 pgs.
"Zinacef (Cefuroxime for Injection)," Glaxosmithkline, Physicians' Desk Reference, Thomson PDR, 2005, 15 pgs.
"Zosyn (Piperacillin and Tazobactam for Injection) Rx Only," Wyeth Pharmaceuticals, Physicians' Desk Reference, Thomson PDR, 2005, 18 pgs.
Thiesen, J. and Kramer, I., "Physico-chemical stability of docetaxel premix solution and docetaxel infusion solutions in PVC bags and polyolefine containers," Pharmacy World & Science, vol. 21, No. 3, 1999, pp. 137-141.
"Prague Hospital Elimiantes PVC IV Bags," Health Care Without Harm, Press release of Arnika, Nov. 20, 2003, 1 pg.
Atkinson, H.C. and Duffull, S.B., "Prediction of drug loss from PVC infusion bags," Journal of Pharmaceutical Pharmacology, vol. 43, 1991, pp. 374-376.
"Efficacy and Safety of Intravenous Nicardipine in the Control of Postoperative Hypertension," The Cardiopulmonary Journal, Chest, vol. 99, No. 2, Feb. 1991, pp. 393-398.
"About Ready-To-Use Systems," web.archive.org, www.baxterbiopharmasolutions.com, Jan. 25, 2005, 2 pgs.
Gupta, P. K., "Solutions and Phase Equilibria," Remington: The Science and Practice of Pharmacy, Ch. 16, 2000, pp. 208-226.
Armstrong, N. A., "Uptake of preservatives by plastic packaging materials," American Cosmetics and Perfumery, vol. 87, Aug. 1972, pp. 45-48.
Avis, K. E. and Levchuk, J.W., "Parenteral Preparations," Remington: The Science and Practice of Pharmacy, Ch. 41, 2000, pp. 780-804.
Craig, S. B., et al., "Stability and compatibility of topotecan hydrochloride for injection with common infusion solutions and containers," Journal of Pharmaceutical and Biomedical Analysis, vol. 16, 1997, pp. 199-205.
Georget, S., "Stability of refrigerated and frozen solutions of tropisetron in either polyvinylchloride or polyolefin infusion bags," Journal of Clincial Phrmacy and Therapeutics, vol. 22, 1997, pp. 257-260.
Green, R., et al., "Use of Di(2-ethylhexyl) Phthalate-Containing Medical Products and Urinary Levels of Mono(2-ethylhexyl) Pthalate in Neonatal Intensive Care Unit Infants," Environmental Health Perspectives, vol. 113, No. 9, Sep. 2005, pp. 1222-1225.
Kay, J., "Toxic agent found in treated newborns is linked to plastic/Bay Area hospitals pressuring suppliers for safer products," San Francisco Gate, Jun. 9, 2005, 6 pgs.
Wigent, R.J., "Chemical Kinetics," Remington: The Science and Practice of Pharmacy, Ch. 19, 2000, pp. 253-274.
Paragraph IV Certification for ANDA No. 203978, dated Aug. 14, 2013.
PDL Biopharma, Inc.; "Cardene IV (nicardipine hydrochloride)," Product Insert, Jan. 2006, USA.
International Search Report and Written Opinion of the International Searching Authority from PCT/US2007/009549, dated Nov. 9, 2007.
Sweetana and Akers, "Solubility principles and practices for parenteral drug dosage form development," PDA J Pharmaceutical Science & Technology, 50(5):330-342 (1996).
Zhang et al., "The use of nicardipine for electroconvulsive therapy: a dose-ranging study," Anesth Analg, vol. 100:378-381 (Feb. 2005).
Endoh et al.. "Effects of nicardipine-, nitroglycerin-, and prostaglandin E1-induced hypotension on human cerebrovascular carbon dioxide reactivity during propofol-fentanyl anesthesia," J Clin Anesth, vol. 11(7):545-549 (Nov. 1999).
Bernard et al., "Long-term hypotensive technique with nicardipine and nitroprusside during isoflurane anesthesia for spinal surgery," Anesth Analg., vol. 75(2):179-185 (Aug. 1992).
Chen et al., "The comparative potentcy of intravenous nicardipine and verapamil on the cardiovascular response to tracheal intubation," Acta Anaesthesiol Sin., vol. 34(4):197-202 (Dec. 1996).
Song et al., "Optimal dose of nicardipine for maintenance of hemodynamic stability after tracheal intubation and skin incision," Anesth Analg, vol. 85:1247-1251 (Dec. 1997).

(56) References Cited

OTHER PUBLICATIONS

Cheung et al., "Acute pharmacokinetic and hemodynamic effects of intravenous bolus dosing of nicardipine," Am Heart J., vol. 119(2 Pt 2):438-442 (Feb. 1990).
Yalkowsky et al., "Formulation-related problems associated with intravenous drug delivery," J Pharm Sciences, vol. 87(7):787-796 (Jul. 1998).
Maurin et al., "Solubilization of nicardipine hydrochloride via complexation and salt formation," J Pharm Sciences, vol. 83(10):1418-1420 (Oct. 1994).
Kaise, B., et al., "Solutions to Health Care Waste: Life-Cycle Thinking and 'Green' Purchasing", Environmental Health Perspectives, vol. 109, No. 3, Mar. 2001, pp. 1-4.
Pomponio, R., et al., "Photostability Studies on Nicardipine-Cyclodextrin Complexes by Capillary Electroporesis", Journal of Pharmaceutical and Biomedical Analysis, vol. 35, 2004, pp. 267-275.
Baaske, M., et al., "Stability of Nicardipine Hydrochoride in Intravenous Solutions", Am J Health-Syst Pharm, vol. 53, Jul. 15, 1996, pp. 1701-1705.
Jenke, et al., "Accumulation of extractables in buffer solutions from a polyolefin plastic container," International Journal of Pharmaceutics, vol. 297, 2005, pp. 120-133.
"Adventist Health System and B. Braun Medical Sign Extended Term Contract for IV System and Infusion Devices," Business Wire, Oct. 19, 2004, 3 pgs.
"Alternatives* to Polyvinyl Chloride (PVC) and Di (2-Ethylhexyl) Phthalate (DEHP) Medical Devices," Going Green: A Resource Kit for Pollution Prevention in Heath Care, Apr. 18, 2005, 8 pgs.
"Alternatives* to Polyvinyl Chloride (PVC) and Di (2-Ethylhexyl) Phthalate (DEHP) Medical Devices," Going Green: A Resource Kit for Pollution Prevention in Heath Care, Sep. 23, 2008, 15 pgs.
"Amerinet and B. Braun Extend Agreement for IV Systems and Supplies," B. Braun/McGaw Company News, Apr. 13, 2000, 1 pg.
"ASHP Guidelines: Minimum Standared for Pharmacies in Hospitals," American Journal Health-Systems Pharmacy Dec. 1, 1995, vol. 52, issue 27, pp. 2711-2717.
"B. Braun Medical Inc. Commends National Institute of Health Expert Panel Meeting on Di(2-ethylhexyl)-phthalate (DEHP)," Business Wire, Oct. 12, 2005, 3 pgs.
"B. Braun Medical, Premier Inc. See Immediate Results from New IV Therapy Products Agreement," Business Wire, Apr. 12, 2004, 3 pgs.
"B. Braun Implements Labeling on Entire Line of PVC-Free and DEHP-Free IV Containers As DEHP Becomes a Growing Concern; California Lists DEHP As a Reproductive Toxicant," Business Wire, Dec. 2, 2003, 3 pgs.
Cummings, et al., "Compatibility of Propranolol Hydrochloride Injection with Intravenous Infusion Fluids in Plastic Containers," American Journal of Hospital Pharmacy, vol. 38, Oct. 1982, pp. 1685-1687.
Cutie, et al., "Compatibility of Verapamil Hydrochloride Injection in Commonly Used Large-volume Parenterals," American Journal Hospital Pharmacy, vol. 37, May 1980, pp. 675-676.
Bellet, et al., "Converting-enzyme inhibition buffers the counter-regulatory response to acute administration of nicardipine," British Journal of Clinical Pharmacology, vol. 24, Oct. 1987, pp. 465-472.
DeLuca, et al., "Formulation of Small Volume Parentals," Pharmaceutical Dosage Forms: Parenteral Medications vol. 1, Second Edition, Marcel Dekker, Inc., 1992, pp. 173-248.
"Draft Position Statement on DEHP in Medical Devices for Stakeholder Consultation," Health Canada, Jan. 2002, 5 pgs.
Aloumanis, et al., "Drug Compatibility with a New Generation of VISIV Pololefin Infusion Solution Containers," International Journal of Pharmaceutical Compounding, vol. 13, No. 2, Mar./Apr. 2009, pp. 162-165.
Trissel, et al., "Drug compatibility with new polyolefin infusion solution containers," American Journal Health-System Pharmacy, vol. 63, Dec. 1, 2006, pp. 2379-2382.

Maurin, et al., "Employing Ionization Behaviors to Resolve a Trace-Level Impurity: Determination of 1 4-Dihydro-2 6-Dimethyl-4-(3-nitrophenyl)-3,5-pyridinedicarboxylic Acid Di-2-[methyl-(phenylmethyl)amino]ethyl Ester in Nicardipine Drug Substance," Pharmaceutical Research, vol. 9, No. 1, Jan. 1992, pp. 1518-1520.
"EXCEL Large Volume Parenterals and PAB Partial Additive Bags Fact Sheet," B. Braun Sharing Expertise, Dec. 25, 2005, 3 pgs.
Jenke, Dennis, "Extractable Substances from Plastic Materials Used in Solution Contact Applications: An Updated Review," Technology Resources, Baxter Healthcare Corporation, PDA Journal Pharmaceutical Science and Technology, vol. 60, No. 3, May/Jun. 2006, pp. 191-207.
Mason, et al., "Factors affecting diazepam infusion: Solubility, administration-set composition, and flow rate," American Journal of Hospital Pharmacy, vol. 38, Oct. 1981, pp. 1449-1454.
"FDA Public Health Notification: PVC Devices containing the Plasticizer DEHP," U.S. Department of Health & Human Services, Jul. 12, 2002, 3 pgs.
"Galaxy Flexible Container," Jan. 25, 2005, 1 pg.
Trissel, Lawrence A., "Nicardipine Hydrochloride AHFS 24:28.08," Handbook on Injectable Drugs 13th Edition, American Society of Health-System Pharmacists, 2005, pp. 1109-1113, 1604, 1621, 1632, 1635 and 1639.
"Why Health Care is Moving Away from the Hazardous Plastic Polyvinyl Chloride (PVC)," Going Green: A Resource Kit for Pollution Prevention in Heath Care, Apr. 6, 2006, 6 pgs.
Bates, et al., "Consensus Development Conference Statement on the Safety of Intravenous Drug Delivery Systems: Balancing Safety and Cost," Hospital Pharmacy, vol. 35, No. 2, Feb. 2000, pp. 150-155.
Moorhatch, et al., "Interactions between drugs and plastic intravenous fluid bags part i: sorption studies on 17 drugs," American Society of Hospital Pharmacists, Inc., vol. 31, Jan. 1974, pp. 72-78.
Moorhatch, et al., "Interactions between drugs and plastic intravenous fluid bags part ii: leaching of chemicals from bags containing various solvent media," American Society of Hospital Pharmacists, Inc., vol. 31, Feb. 1974, pp. 149-152.
Lee, et al., "An intravenous formulation decision tree for discovery compound formulation development," International Journal of Pharmaceutics vol. 253, Mar. 6, 2003, pp. 111-119.
Gouyon, et al., "Intravenous nicardipine in hypertensive preterm infants," Archives of Disease in Childhood Fetal & Neonatal Edition, Mar. 1997, vol. 76, pp. F126-F127.
Intravia Flexible Container, Jan. 25, 2005, 1 pg.
Shader, et al., "It's in the Bag: Drug Absorption of Drug-Delivery Systems," Journal of Clinical Psychopharmacology, vol. 17, No. 5, Oct. 1997; pp. 339-340.
Kim, et al., "Nicardipine Hydrochloride Injectable Phase IV Open-Label Clinical Trial: Study on the Anti-Hypertensive Effect and Safety of Nicardipine for Acute Aortic Dissection," Journal of International Medical Research, vol. 30, Jun. 2002 pp. 337-345.
"Looking for extra power to overcome market challenges?" Baxter, Dec. 2003, 8 pgs.
U.S. Appl. No. 12/971,084—Response/Amendment dated Feb. 28, 2013.
U.S. Appl. No. 12/971,084—Non-Final Rejection dated Nov. 30, 2012.
U.S. Appl. No. 12/645,169—Response/Amendment dated Feb. 6, 2013.
U.S. Appl. No. 12/645,169—Non-Final Rejection dated Sep. 6, 2012.
Yang et al., "Nicardipine versus nitroprusside infusion as antihypertensive therapy in hypertensive emergencies," J. Int Med Research, vol. 32(2):118-123 (Mar.-Apr. 2004).
Atlee et al., "The use of esmolol, nicardipine, or their combination to blunt hemodynamic changes after laryngoscopy and tracheal intubation," Anesth Analg, vol. 90:280-285 (Feb. 2000).
Aya et al., "Intravenous nicardipine for severe hypertension in pre-eclampsia—effects of an acute treatment on mother and foetus," Intensive Care Med., vol. 25(11):1277-1281 (Nov. 1999).
Cheung et al., "Nicardipine intravenous bolus dosing for acutely decreasing arterial blood pressure during general anesthesia for

(56) References Cited

OTHER PUBLICATIONS cardiac operations: pharmacokinetics, pharmacodynamics, and associated effects on left ventricular function," Anesth Analg, vol. 89:1116-1123 (Nov. 1999).

Colson et al., "Haemodynamic heterogeneity and treatment with the calcium channel blocker nicardipine during phaeochromocytoma surgery," Act Anaesthesiol Scand., vol. 42(9):1114-1119 (Oct. 1998).

Elatrous et al., "Short-term treatment of severe hypertension of pregnancy: prospective comparison of nicardipine and labetalol," Intensive Care Med., vol. 28(9):1281-1286 (Jul. 26, 2002).

Fernandes et al., "Physiochemical characterization and in vitro dissolution behavior of nicardipine-cyclodextrins inclusion compounds," Eur. J. of Pharma. Sci. 15: pp. 79-88, 2002.

Flynn et al., "Intravenous nicardipine for treatment of severe hypertension in children," J Pediatr., vol. 139(1):38-43 (Jul. 2001).

Kwak et al., "Comparison of the effects of nicardipine and sodium nitroprusside for control of increased blood pressure after coronary artery bypass graft surgery," J Int Med Res, vol. 32:342-350 (Jul.-Aug. 2004).

Vincent et al., "Intravenous nicardipine in the treatment of postoperative arterial hypertension," J Cardiothorac Vasc Anesth, vol. 11(2):160-164 (Apr. 1997).

International Preliminary Report on Patentability for PCT/US2007/066897, dated Jan. 13, 2009.

International Search Report for PCT/US2007/066897, published Feb. 19, 2009.

Written Opinion of the International Searching Authority for PCT/US2007/066897, dated Nov. 24, 2008.

International Preliminary Report on Patentability for PCT/US2007/009549, dated Oct. 22, 2008.

International Search Report for PCT/US2007/009549, published Jan. 3, 2008.

Written Opinion of the International Searching Authority for PCT/US2007/009549 (date not indicated).

Non Final Office Action for U.S. Appl. No. 11/737,067, dated Oct. 29, 2008.

Complaint 1:13-cv-01275-GMS (Jul. 24, 2013).

Answer 1:13-cv-01275-GMS (Aug. 9, 2013).

Complaint 1:13-cv-05723-NLH-AMD (Sep. 25, 2013).

Answer and Counterclaims 1:13-cv-05723-NLH-AMD (Nov. 6, 2013).

* cited by examiner

PRE-MIXED, READY-TO-USE PHARMACEUTICAL COMPOSITIONS

1. CROSS REFERENCE TO RELATED APPLICATIONS

This application is a continuation of U.S. patent application Ser. No. 15/159,495 filed on May 19, 2016, which is a continuation of U.S. patent application Ser. No. 12/977,965 filed on Dec. 23, 2019, now issued as U.S. Pat. No. 9,370,586, which is a continuation of U.S. patent application Ser. No. 12/645,169, filed on Dec. 22, 2009, now issued as U.S. Pat. No. 9,364,564, which is a continuation of U.S. patent application Ser. No. 12/407,557 filed on Mar. 19, 2019, now issued as U.S. Pat. No. 7,659,291, which is a divisional of U.S. patent application Ser. No. 11/788,076, filed on Apr. 18, 2007, now issued as U.S. Pat. No. 7,612,102, which claims benefit under 35 U.S.C. § 119(e) to U.S. Provisional application Ser. No. 60/793,074, filed Apr. 18, 2006, the contents of which are incorporated herein by reference.

2. BACKGROUND

Nicardipine hydrochloride ((±)-2-(benzyl-methyl amino) ethyl methyl 1,4-dihydro-2,6-dimethyl-4-(m-nitrophenyl)-3,5-pyridinedicarboxylate monohydrochloride) is a calcium ion influx inhibitor useful for the treatment of cardiovascular and cerebrovascular disorders (see, e.g., U.S. Pat. No. 3,985,758). Nicardipine hydrochloride is currently sold in capsule form and in an injectable intravenous form. The capsule form is marketed as CARDENE® and is available as an immediate release oral capsule and as an extended release oral capsule. The injectable intravenous form of CARDENE® is marketed in glass ampuls suitable for intravenous administration following dilution in a compatible intravenous fluid, such as dextrose or sodium chloride (CARDENE® I.V.). Each milliliter of a CARDENE® I.V. ampul contains 2.5 mg nicardipine hydrochloride in water, 48.0 mg sorbitol, buffered to pH 3.5 with 0.525 mg citric acid monohydrate and 0.09 mg sodium hydroxide. For infusion, each milliliter of the diluted formulation contains 0.1 mg of nicardipine hydrochloride, with a variable pH due to the diluent selected by the end user. U.S. Reissue Pat. No. RE. 34,618 (a reissue of U.S. Pat. No. 4,880,823) describes an injectable composition of nicardipine hydrochloride that is stored in a light resistant brown ampul. U.S. Pat. No. 5,164,405 describes a buffered pharmaceutical composition containing nicardipine designed for parenteral administration, that is also stored in an ampul.

The requirement for diluting CARDENE® I.V. before use is associated with a number of disadvantages. One disadvantage is that the diluted solution is only stable for 24 hours at room temperature. Another disadvantage is that the pH of the diluted formulation varies depending on the choice of diluent. Since CARDENE® I.V. can be used under emergency conditions to control blood pressure, dilution of the concentrated ampul formulation consumes valuable time that could be used to treat a patient. Other disadvantages associated with the dilution step include the potential for contamination, dosage errors, and safety hazards associated with the use of glass ampuls.

The pharmaceutical compositions and methods described herein overcome these disadvantages. In particular, the ready-to-use, injectable formulations described herein are stable, allow medical personal to use prepared containers containing an injectable formulation off the shelf without additional preparation, avoid potential contamination problems, and eliminate dosage errors.

3. SUMMARY

Described herein are ready-to-use, premixed pharmaceutical compositions of nicardipine or pharmaceutically acceptable salts thereof, which are suitable for continuous intravenous infusion. By providing ready-to-use, premixed pharmaceutical compositions with a buffered pH, these pharmaceutical compositions are stable at room temperature for at least one year. When stored at room temperature, the pharmaceutical compositions exhibit between 0% to about 15% loss of drug and between 0% to about 3% (w/w) total impurity formation over an eighteen to twenty four month period.

Additional benefits of the pre-mixed, ready-to-use, injectable pharmaceutical compositions include convenience and ease of use as compared to an ampul formulation, improved safety for patients due to elimination of dosage errors and solution contamination, reduction of medical waste, and ease of administration in emergency situations.

The present disclosure relates to premixed pharmaceutical compositions comprising nicardipine or pharmaceutically acceptable salts thereof, one or more tonicity agents, and a buffer. In some embodiments, the compositions optionally comprise one or more cosolvents. Nicardipine hydrochloride can be present at concentrations between about 0.05 mg/ml to about 15 mg/ml. Typically, the concentration range for nicardipine hydrochloride is between about 0.1 mg/ml to about 0.2 mg/ml. Optionally, the pharmaceutical compositions can comprise acids and bases.

The pharmaceutical compositions described herein require no dilution prior to administration and typically have a pH within the range from about 3.6 to about 4.7. The compositions can be administered by parenteral routes, including, subcutaneous, intramuscular, intravenous, intra-atrial, or intra-arterial continuous infusion to a patient. The compositions are suitable for the short-term treatment of hypertension when oral therapy is not feasible or desirable.

Methods for making a premixed nicardipine hydrochloride formulation suitable for intravenous administration comprise the steps of providing an effective amount of nicardipine hydrochloride in a solution comprising one or more tonicity agents, a buffer, and, optionally, one or more cosolvents. Sufficient water is added to make up the final volume. If required, the pH of the solution can be adjusted using a suitable pH adjuster. The compositions are dispensed in pharmaceutically acceptable containers for storage and direct administration to patients.

4. BRIEF DESCRIPTION OF THE FIGURES

FIG. 1 provides a diagrammatic illustration of the effect of various diluents on the pH and stability of an ampul formulation post dilution over a twenty four hour period at room temperature.

Figure 2A:
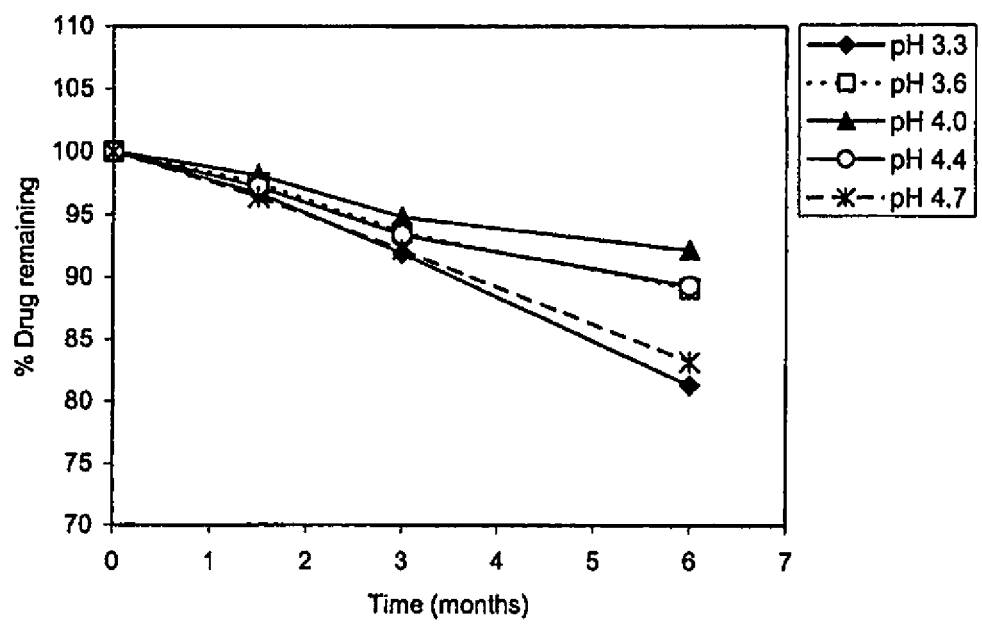
Figure 2B:
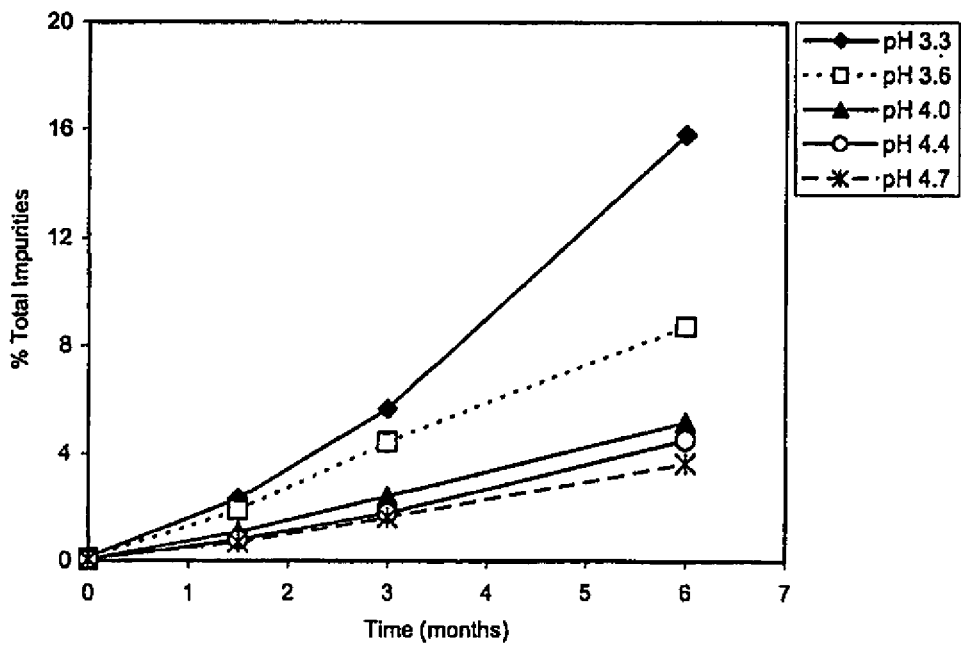
Figure 3A:
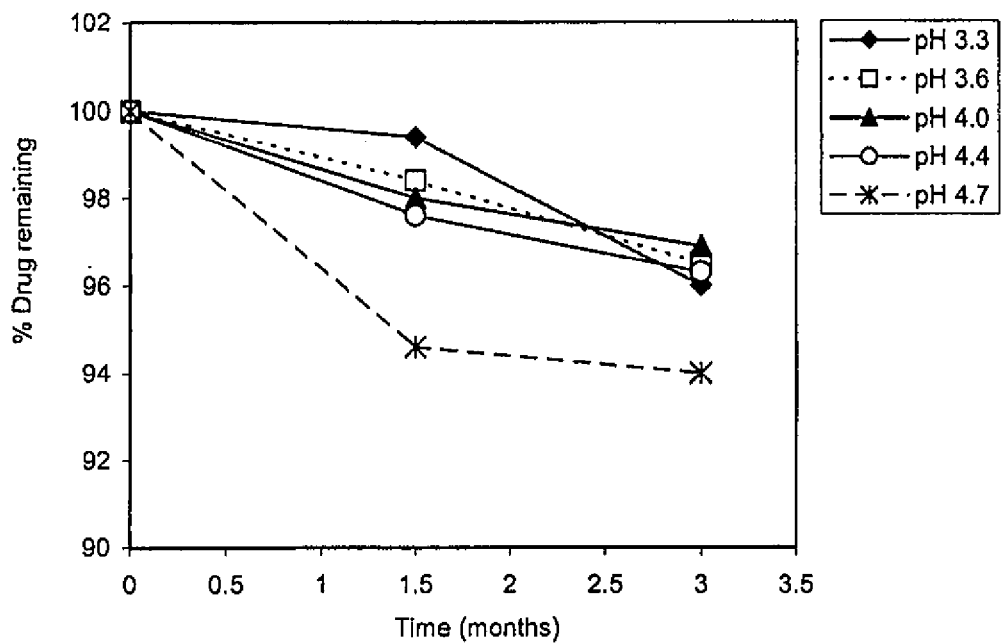
Figure 3B:
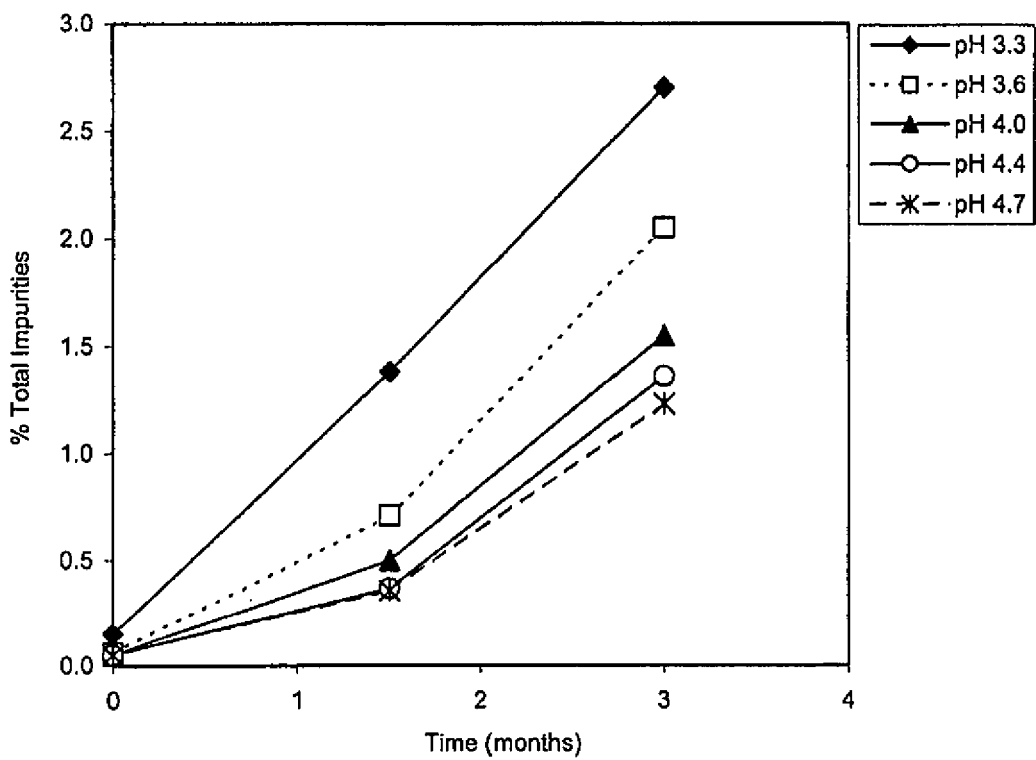
Figure 4A:
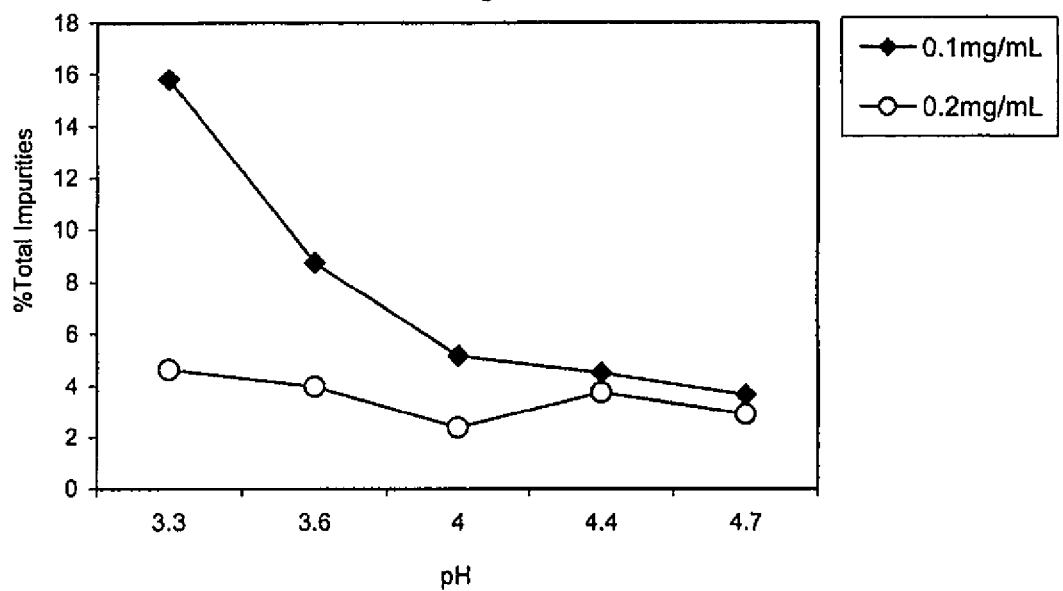
Figure 4B:
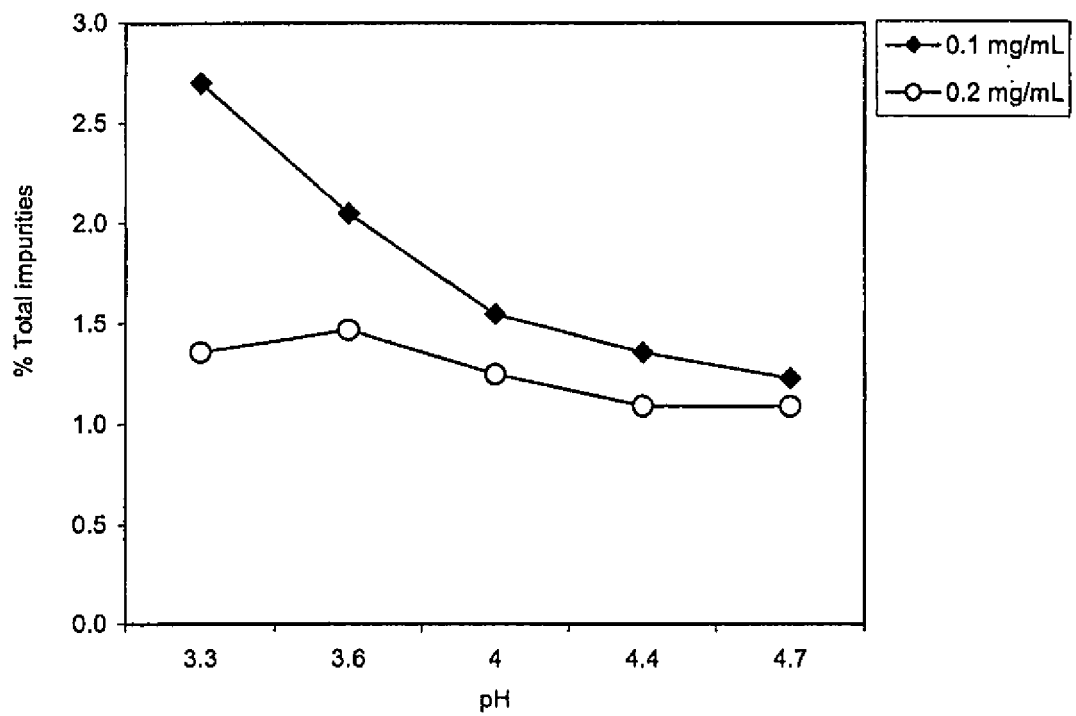
Figure 5A:
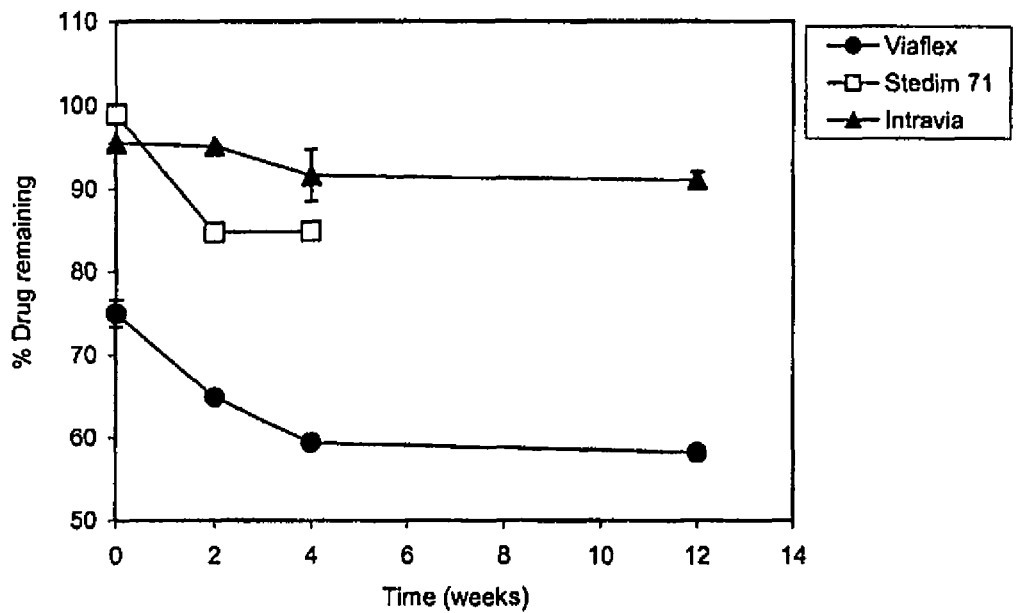
Figure 5B:
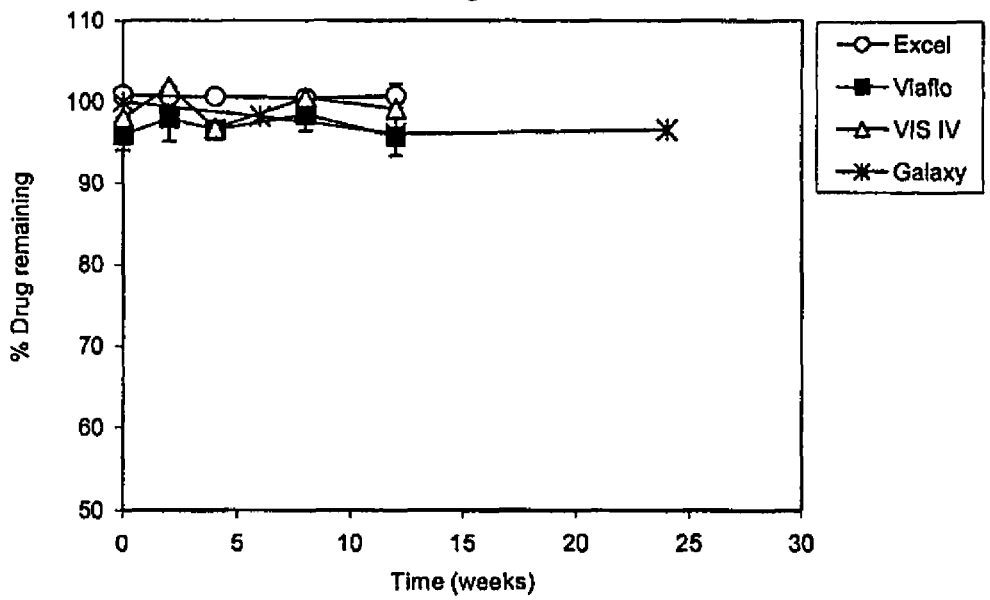

FIGS. 2A and 2B provide a diagrammatic illustration of the effect of pH on drug loss (FIG. 2A) and total impurity formation (FIG. 2B) in a premixed non-sorbitol formulation comprising 0.1 mg/ml nicardipine hydrochloride, 0.1 mM citric acid and 5% dextrose at 40° C.;

FIGS. 3A and 3B provide a diagrammatic illustration of the effect of pH on drug loss (FIG. 3A) and total impurity formation (FIG. 3B) in a premixed non-sorbitol formulation comprising 0.1 mg/ml nicardipine hydrochloride, 0.1 mM citric acid and 0.9% saline at 40° C.;

FIGS. 4A and 4B provide a diagrammatic illustration of the effect of nicardipine concentration on impurity formation in non-sorbitol dextrose formulations comprising 0.1 mg/ml nicardipine hydrochloride, 0.1 mM citrate, 5% dextrose, or 0.2 mg/ml nicardipine hydrochloride, 0.2 mM citrate and 5% dextrose after six months at 40° C. (FIG. 4A); and, in non-sorbitol saline formulations comprising 0.1 mg/ml nicardipine hydrochloride, 0.1 mM citrate, 0.9% saline, or 0.2 mg/ml nicardipine hydrochloride, 0.2 mM citrate and 0.9% saline after 3 months at 40° C. (FIG. 4B); and FIGS. 5A and 5B provide a diagrammatic illustration of the effect of incompatible (FIG. 5A) and compatible (FIG. 5B) plastic film composition on product stability at 40° C. in a premixed non-sorbitol formulation comprising 0.2 mg/ml nicardipine HCL, 0.2 mM citric acid, S % dextrose, at a pH of 4.0 to 4.2.

5. DETAILED DESCRIPTION

The premixed pharmaceutical compositions described herein comprise nicardipine or a pharmaceutically acceptable salt thereof as the active ingredient, at least one tonicity agent and a buffer. As used herein, the term "pre-mixed" refers to a pharmaceutical composition that does not require reconstitution or dilution before administration to a patient. In contrast to ampul formulations comprising nicardipine hydrochloride that must be diluted prior to use in a diluent and container selected by hospital personnel, the premixed pharmaceutical compositions provided herein are stable at room temperature for 6 months or longer due to the inclusion of a buffer capable of maintaining the pH within an optimal pH range, which is typically between 3.6 to about 4.7. In some embodiments, suitable pH adjusters and/or cosolvents are added to the pharmaceutical compositions.

5.2 Premixed Pharmaceutical Compositions

The production of stable, ready-to-use, premixed pharmaceutical compositions comprising nicardipine and/or its pharmaceutically acceptable salts as the active ingredient presents different development hurdles than does the development of the concentrated ampul product sold commercially as CARDENE® I.V. As shown in FIG. 1, the percent of nicardipine remaining in solution decreases as function of pH over a twenty-four hour period. The percent decrease in nicardipine varies with the diluent and container chosen by the hospital staff.

As described in the Examples, pH (see, also, e.g., FIGS. 2A, 2B, 3A and 3B), the concentration of the active ingredient (see, also, e.g., FIGS. 4A and 4B), and the composition of the container material (see, also, e.g., FIGS. 5A and 5B) affect the stability of the active ingredient and the formation of impurities. Thus, the development of a stable, ready-to-use premixed pharmaceutical composition requires simultaneous optimization of pH and nicardipine hydrochloride concentration, as well as selection of a pharmaceutically compatible container. The ready-to-use pharmaceutical compositions described herein exhibit 0% to 15% drop in drug concentration and 0% to 3% formation of impurities when maintained at room temperature for 6 to at least 24 months. Typically, the pharmaceutical compositions are stable when maintained at room temperature for at least 6 months, at least 12 months, at least 18 months, and at least 24 months. The compositions are also stable over extended periods of time when maintained at temperatures from about 2° to 8° C. The term "stable", as used herein, means remaining in a state or condition that is suitable for administration to a patient.

Compounds for use according to the compositions and methods described herein that can contain one or more asymmetric centers can occur as racemates, racemic mixtures, and as single enantiomers. Accordingly, the compositions and methods described herein are meant to comprehend all isomeric forms of such compounds.

The premixed pharmaceutical compositions described herein comprise nicardipine and/or its pharmaceutically acceptable salts. Nicardipine, its pharmaceutically acceptable salts, preparation, and use are known in the art (see, e.g., U.S. Pat. No. 3,985,758, incorporated herein by reference in its entirety). Examples of pharmaceutically acceptable salts of nicardipine include hydrochlorides, sulfates, phosphates, acetates, fumarates, maleates and tartrates.

Typically, the premixed pharmaceutical compositions comprise 0.05-15 mg/ml nicardipine or a pharmaceutically acceptable salt thereof. For example, suitable concentrations of nicardipine or a pharmaceutically acceptable salt thereof, include, but are not limited to: 0.05-0.1 mg/ml, 0.1-15 mg/ml, 0.1-10 mg/ml, 0.1-5 mg/ml, 0.1-3.0 mg/ml, 0.1-2.0 mg/ml, 0.1-1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml or 0.1 mg/ml.

In some embodiments, the premixed pharmaceutical compositions comprise nicardipine hydrochloride as the active ingredient at a concentration sufficient to permit intravenous administration at a concentration between 0.1 mg/ml to 0.2 mg/ml. In some embodiments, the concentration of nicardipine hydrochloride suitable for use in the compositions and methods described herein includes, but is not limited to, at least about 0.1 mg/ml. In other embodiments, the concentration of nicardipine hydrochloride suitable for use in the compositions and methods described herein includes, but is not limited to, at least about 0.2 mg/ml.

In some embodiments, the premixed formulation comprises, in addition to nicardipine and/or its pharmaceutically acceptable salts, a buffer that has sufficient buffering capacity to maintain the desired pH range throughout the shelf-life of the product. As shown in FIGS. 2A and 2B, pH is important for the long term stability of nicardipine in the premixed pharmaceutical compositions. Although the pH of the premixed pharmaceutical compositions can range from between about 3.0 to about 7.0, pharmaceutical compositions having a pH within the range of about 3.6 to about 4.7 exhibit a lower percentage of drug degradation and total impurities (See FIGS. 2A, 2B, 3A and 3B). Accordingly, suitable pH ranges for use in the premixed pharmaceutical compositions include, but are not limited to, pH range of at least about 3.0, at least about 3.1, at least about 3.2, at least about 3.3, at least about 3.4, at least about 3.5, at least about 3.6, at least about 3.7, at least about 3.8, at least about 3.9, at least about 4.0, at least about 4.1, at least about 4.2, at least about 4.3, at least about 4.4, at least about 4.5, at least about 4.6, at least about 4.7, at least about 4.8, at least about 4.9, at least about 5.0, at least about 5.2, at least about 5.5, at least about 6.0, at least about 6.5, at least about 7.0.

In some embodiments, the pH of the premixed pharmaceutical compositions is between about 3.0 to about 5.0. In other embodiments, the pH of the premixed pharmaceutical compositions is between about 3.6 to about 4.7. In other embodiments, the pH of the premixed pharmaceutical compositions is between about 4.0 to about 4.4. In yet other embodiments, the pH of the premixed pharmaceutical compositions is 4.2.

Buffers suitable for use in the pharmaceutical compositions described herein include, but are not limited to, pharmaceutically acceptable salts and acids of acetate, glutamate, citrate, tartrate, benzoate, lactate, histidine or other amino acids, gluconate, phosphate, malate, succinate, formate, propionate, and carbonate. "Pharmaceutically acceptable" is used herein in the sense of being compatible with the other ingredients of the formulation and not deleterious to the recipient thereof. Accordingly, the term "pharmaceutically acceptable salt" references salt forms of the active compounds which are prepared with counter ions which are non-toxic under the conditions of use and are compatible with a stable formulation. The concentration of the buffer in the formulation can be expressed in mg/ml, g/L or as a molar concentration. In typical embodiments, from about 0.0001 mg/ml to about 100 mg/ml of a suitable buffer is present in the pharmaceutical compositions. Thus, the premixed pharmaceutical compositions can comprise from about 0.001 to about 0.01 mg/ml of a suitable buffer, from about 0.01 to about 0.01 mg/ml of a suitable buffer, from about 0.01 to about 0.1 mg/ml of a suitable buffer, from about 0.1 to 1 mg/ml of a suitable buffer, from about 1 to about 5 mg/ml of a suitable buffer, from about 5 to about 10 mg/ml of a suitable buffer, from about 10 to about 15 mg/ml of a suitable buffer, from about 15 to about 20 mg/ml of a suitable buffer, from about 20 to about 25 mg/ml of a suitable buffer, from about 25 to about 50 mg/ml of a suitable buffer, from about 50 to about 75 mg/ml of a suitable buffer, and from about 75 to about 100 mg/ml of a suitable buffer.

Alternatively, the buffer concentration can be expressed as molar concentrations. In typical embodiments, from about 0.1 to 100 mM of a suitable buffer is present in the pharmaceutical compositions. Thus, the premixed pharmaceutical compositions can comprise a suitable buffer having a concentration from about 0.1 to about 100 mM, from about 0.1 to about 0.5 mM, from about 0.5 to about 1.0 mM, from about 1.0 to about 5 mM, from about 5 to about 10 mM, from about I 0 to about 15 mM, from about 15 to about 25 mM, from about 25 to about 50 mM, from about 50 to about 75 mM, and from about 75 to about 100 mM.

n some embodiments, the premixed pharmaceutical compositions further comprise a pH adjuster. Suitable pH adjusters typically include at least an acid or a salt thereof, and/or a base or a salt thereof. Acids and bases can be added on an as needed basis in order to achieve a desired pH. For example, if the pH is greater than the desired pH, an acid can be used to lower the pH to the desired pH. Acids suitable for use in premixed pharmaceutical compositions include, but are not limited to, hydrochloric acid, phosphoric acid, citric acid, ascorbic acid, acetic acid, sulphuric acid, carbonic acid and nitric acid. In some embodiments, hydrochloric acid is used to adjust the pH. By way of another example, if the pH is less than the desired pH, a base can be used to adjust the pH to the desired pH. Bases suitable for use in premixed pharmaceutical compositions include, but are not limited to, sodium hydroxide, potassium hydroxide, calcium hydroxide, sodium carbonate, sodium citrate, sodium acetate, and magnesium hydroxide. In some embodiments, sodium hydroxide is used to adjust to pH.

In some embodiments, the premixed pharmaceutical compositions further comprise one or more tonicity agents. Typically, tonicity agents are used to adjust the osmolality of the premixed pharmaceutical compositions to bring it closer to the osmotic pressure of body fluids, such as blood or plasma. In some embodiments the tonicity of the premixed formulation can be modified by adjusting the concentration of buffer and/or other components present in the premixed formulation.

Provided that the compositions are physiologically compatible, the compositions do not require any particular osmolality. Thus, the compositions can be hypotonic, isotonic or hypertonic. Typically the premixed pharmaceutical compositions have a tonicity between about 250 to about 350 mOsm/kg.

Suitable tonicity agents for use in the premixed pharmaceutical compositions include, but are not limited to, anhydrous or hydrous forms of sodium chloride, dextrose, sucrose, xylitol, fructose, glycerol, sorbitol, mannitol, potassium chloride, mannose, calcium chloride, magnesium chloride and other inorganic salts. The quantity of the tonicity agent in the formulation can be expressed in mg/ml or in g/L. In typical embodiments, the tonicity agent(s) is present from about 1 mg/ml to about 90 mg/ml. Thus, the premixed pharmaceutical compositions can comprise one or more tonicity agents at about 1-5 mg/ml, at about 5-10 mg/ml, at about 10-15 mg/ml, at about 15-25 mg/ml, at about 25-50 mg/ml, at about 50-60 mg/ml, at about 60-70 mg/ml, at about 70-80 mg/ml, and at about 80 to 90 mg/ml, as well as combinations of the above ranges.

Alternatively, the tonicity agent concentration is measured in weight/volume percent. In typical embodiments, the tonicity agent(s) is present from about 0.1% to about 10%. For example, suitable tonicity agent concentrations include, but are not limited to, from about 0.1% to about 0.2%, from about 0.2% to about 0.3%, from about 0.3% to about 0.4%, from about 0.4% to about 0.5%, from about 0.5% to about 0.6%, from about 0.6% to about 0.7%, from about 0.7% to about 0.8%, from about 0.8% to about 0.9%, from about 0.9% to about 1%, from about I % to about 2%, from about 2% to about 3%, from about 3% to about 4%, from about 4% to about 5%, from about 5% to about 6%, from about 6% to about 7%, from about 7% to about 8%, from about 8% to about 9%, and from about 9% to about 10%, as well as combinations of the above ranges.

In some embodiments, the tonicity agent is dextrose. Typically, the concentration of dextrose suitable for use in the premixed pharmaceutical compositions is between about 2.5% (w/v) to about 7.5%. By way of example, suitable dextrose concentrations include, but are not limited to, from about 2.5% to about 3%, from about 3% to about 3.5%, from about 3.5% to about 4% (which is equivalent to about 40 mg/ml), from about 4% to about 4.5%, from about 4.5% to about 5% (which is equivalent to about 50 mg/ml), from about 5% to about 5.5%, from about 5.5% to about 6% (which is equivalent to about 60 mg/ml), from about 6% to about 6.5%, from about 6.5% to about 7%, as well as combinations of the above ranges.

In some embodiments, the tonicity agent is sodium chloride. Typically, the concentration of sodium chloride suitable for use in the premixed pharmaceutical compositions is between about 0.1% (w/v) to about 1.8%. By way of example, suitable sodium chloride concentrations include, but are not limited to, from about 0.1% to about 0.2%, from about 0.2% to about 0.3%, from about 0.3% to about 0.4%, from about 0.4% to about 0.5%, from about 0.5% to about 0.6%, from about 0.6% to about 0.7%, from about 0.7% to about 0.8% (which is equivalent to 8 mg/ml), from out 0.8% to about 0.9% (which is equivalent to 9 mg/ml), from about 0.9% to about 1.0%, from about 1% to about 1.2%, from 1.2% (which is equivalent to 12 mg/ml) to about 1.4%, from about 1.4% to about 1.6%, and from about 1.6% to about 1.8%.

In some embodiments, the premixed pharmaceutical compositions comprise two, three, four, or more tonicity agents. In these embodiments, the concentration of each tonicity agent is typically less than the concentration that is used when only a single agent is present in the premixed formulation. For example, if the premixed formulation comprises sorbitol at 1.92 mg/ml, a suitable concentration of sodium chloride is 8.6 mg/ml. By way of another example, if the premixed formulation comprises 1.92 mg/ml sorbitol, a suitable concentration of dextrose is 48 mg/ml.

In some embodiments, the premixed pharmaceutical compositions further comprise one or more cosolvents. A "cosolvent" is a solvent which is added to the aqueous formulation in a weight amount which is less than that of water and assists in the solubilization of nicardipine and/or a pharmaceutically acceptable salt thereof, enhances stability of the premixed formulation, and/or adjusts the osmolality of the premixed pharmaceutical compositions. Cosolvents suitable for use in the premixed pharmaceutical compositions include, but are not limited to, glycols (e.g., polyethylene glycol, propylene glycol), ethanol, and polyhydric alcohols (e.g., sorbitol, mannitol, xylitol).

The quantity of the cosolvent used in the formulation can be expressed in mg/ml or in g/L. In typical embodiments, the cosolvent(s) is present from about 1 mg/ml to about 100 mg/ml. Thus, the premixed pharmaceutical compositions can comprise one or more cosolvent(s) at about 1 to about 2 mg/ml, at about 2 to about 3 mg/ml, at about 3 to about 4 mg/ml, at about 4 to about 5 mg/ml, at about 5 to about 10 mg/ml, at about 10 to about 15 mg/ml, at about 15 to about 25 mg/ml, at about 25 to about 50 mg/ml, at about 50 to about 60 mg/ml, at about 60 to about 70 mg/ml, at about 70 to about 80 mg/ml, at about 80 to 90 mg/ml, and at about 90 to 100 mg/ml, as well as combination of the above ranges.

Alternatively, the cosolvent concentration is measured in weight/volume percent. In typical embodiments, the cosolvent(s) is present from about 0.1% to about 25%. For example, suitable cosolvent concentrations include, but are not limited to, at least about 0.1% to 0.3%, from about 0.3% to about 0.5%, from about 0.5% to about 0.7%, from about 0.7% to about 0.9%, from about 0.9% to about 1%, from about 1% to about 3%, from about 3% to about 5%, from about 5% to about 7%, from about 7% to about 9%, from about 9% to about 11%, from about 11% to about 13% from about 13% to about 15%, from about 15% to about 20%, and from about 20% to about 25%, as well as combination of the above ranges.

In some embodiments, the premixed pharmaceutical compositions further comprise one or more cyclodextrins. Due to their structure, cyclodextrins have the ability to form complexes, or inclusion complexes, with a variety of organic and inorganic molecules. Complexes of nicardipine with cyclodextrins have been described (see, e.g., U.S. Pat. No. 5,079,237 which describes an inclusion complex of nicardipine or its hydrochloride with alpha-cyclodextrin, beta-cyclodextrin or gamma-cyclodextrin; U.S. Pat. No. 5,519,012 which describes inclusion complexes of dihydropyridines, including nicardipine, with hydroxy-alkylated-β-cyclodextrins; and, U.S. Pat. No. 5,904,929 which describes numerous drugs in a pharmaceutical composition with per-C2-18 acylated cyclodextrins). None of the above references discloses a dihydropyridine in combination with a cyclodextrin comprising a sulfate group. An example of a commercially available sulfated cyclodextrin is CAPTISOL®. CAPTISOL® is a polyanionic-cyclodextrin derivative with a sodium sulfonate salt that is separated from the lipophilic cavity by a butyl ether spacer group, or sulfobutylether. Methods for making the sulfoalkyl ether cyclodextrin derivatives are welllmown in the art and are taught in U.S. Pat. No. 5,376,645. Methods for forming complexes of the derivatives with a drug are also welllmown in the art as disclosed in U.S. Pat. No. 5,376,645.

The cyclodextrin concentration can be measured in weight/volume percent. In typical embodiments, cyclodextrin(s) is present from about 0.1% to about 25%. For example, suitable cyclodextrin(s) concentrations include, but are not limited to, at least about 0.1% to 0.3%, from about 0.3% to about 0.5%, from about 0.5% to about 0.7%, from about 0.7% to about 0.9%, from about 0.9% to about 1%, from about 1% to about 3%, from about 3% to about 5%, from about 5% to about 7%, from about 7% to about 9%, from about 9% to about 11%, from about 11% to about 13% from about 13% to about 15%, from about 15% to about 20%, and from about 20% to about 25%.

Examples of stable, premixed pharmaceutical compositions comprising the active ingredient, a tonicity agent, a buffer and optionally, a cosolvent are shown in Table 1.

TABLE 1

| Active Ingredient | Tonicity Agent(s) (mg/ml) | Buffer (mg/ml) | Cosolvent (mg/ml) | pH |
|---|---|---|---|---|
| nicardipine hydrochloride (0.1 mg/ml) | NaCl (8.6 mg/ml) | Citric acid, anhydrous (0.0192 mg/ml) | Sorbitol (1.92 mg/ml) | 3.6-4.7 |
| nicardipine hydrochloride (0.1 mg/ml) | Dextrose, hydrous (48 mg/ml) | Citric acid, anhydrous (0.0192 mg/ml) | Sorbitol (1.92 mg/ml) | 3.6-4.7 |
| nicardipine hydrochloride (0.1 mg/ml) | NaCl (9 mg/ml) | Citric acid, anhydrous (0.0192 mg/ml) | None | 3.6-4.7 |
| nicardipine hydrochloride | Dextrose, hydrous (50 mg/ml) | Citric acid, anhydrous (0.0192 mg/ml) | None | 3.6-4.7 |
| nicardipine hydrochloride (0.2 mg/ml) | NaCl (9 mg/ml) | Citric acid, anhydrous (0.0384 mg/ml) | None | 3.6-4.7 |
| nicardipine hydrochloride (0.2 mg/ml) | Dextrose, hydrous (50 mg/ml) | Citric acid, anhydrous (0.0384 mg/ml) | None | 3.6-4.7 |
| nicardipine hydrochloride (0.2 mg/ml) | NaCl (8.3 mg/ml) | Citric acid, anhydrous (0.0384 mg/ml) | Sorbitol (3.84 mg/ml) | 3.6-4.7 |
| nicardipine hydrochloride (0.2 mg/ml) | Dextrose, hydrous (46 mg/ml) | Citric acid, anhydrous (0.0384 mg/ml) | Sorbitol (3.84 mg/ml) | 3.6-4.7 |

In some embodiments, the pharmaceutical compositions are any as described in U.S. Provisional Application Ser. No. 60/793,084, filed Apr. 18, 2006, which is incorporated herein by reference.

5.3 Methods

The order in which various components comprising the compositions is added to the buffered solution is not critical, provided that the resulting compositions are stable and are suitable for continuous intravenous infusion. Accordingly, the compositions described herein can be made by prepared in a number of different ways. For example, in some embodiments, the compositions can be prepared by adding buffer, a tonicity agent and/or a cosolvent to water; adding nicardipine to the buffered water solution; adding an pH adjuster to achieve the desired pH; and then adding sufficient water to make up the final volume. If necessary, the pH can be readjusted to achieve the desired pH range. By way of another example, the compositions can be prepared by adding buffer and nicardipine or a pharmaceutically acceptable salt thereof to water; adding a tonicity agent and/or cosolvent, adjusting the pH to achieve the desired pH range; and then adding sufficient water to make up the final volume. By way of another example, a cosolvent can be added prior to the addition of nicardipine or a pharmaceutically acceptable salt thereof, and a tonicity agent can be added after the addition of nicardipine or a pharmaceutically acceptable salt thereof. By way of another example, a tonicity agent can be added prior to the addition of nicardipine or a pharmaceutically acceptable salt thereof, and a cosolvent can be added after the addition of nicardipine or a pharmaceutically acceptable salt thereof. By way of another example, the compositions can be prepared by adding buffer, tonicity agent and/or cosolvent to water; adjusting the pH to a first pH range suitable for dissolving nicardipine (for example, less than pH 3.6); adding nicardipine or a pharmaceutically acceptable salt thereof; adjusting the pH to achieve the desired final pH range; and then adding sufficient water to make up the final volume.

In some embodiments, pharmaceutical compositions comprising nicardipine hydrochloride, dextrose, and citric buffer at pH 3.6-4.7 can be prepared by adding citric acid to water, adding dextrose to the buffered water, adding nicardipine hydrochloride to the buffered water solution, adjusting the pH if necessary to the range 3.6-4.7, and adding sufficient water to make up the final volume. If necessary, the pH can be readjusted to between about 3.6 to about 4.7.

In some embodiments, pharmaceutical compositions comprising nicardipine hydrochloride, sodium chloride, and citrate buffer at pH 3.6 to about 4.7 can be prepared by adding citric acid to water, adding nicardipine to the buffered water solution, adding sodium chloride to the buffered water solution, adjusting the pH to between about 3.6 to about 4.7, and adding sufficient water to make up the final volume. If sorbitol is included in the formulation, sorbitol is added at the same time as the citric acid.

In some embodiments, the pharmaceutical compositions can be prepared by adding nicardipine or a pharmaceutically acceptable salt thereof to an acidic solution having a pH less than 5.0. For example, the acidic solution can be prepared by adding an acidic component of a buffer system. A buffer, one or more tonicity agents, and/or cosolvents can be added to the acidic solution before or after dissolving the nicardipine. Sufficient water is then added to make up the final volume. If necessary, the pH of the composition can be adjusted to between about 3.6 to about 4.7.

In some embodiments, the pharmaceutical compositions can be made by adding nicardipine or a pharmaceutically acceptable salt thereof to a solution that has been heated to a temperature greater than 35° C.; adding buffer, one or more tonicity agents, and/or cosolvents to the acidic solutions; and adding sufficient water to make up the final volume. If necessary, the pH of the composition can be adjusted to between about 3.6 to about 4.7.

The pharmaceutical compositions can be packaged for use in a variety of containers. The compositions are preferably packaged in a pharmaceutically acceptable container, such as an intravenous bag or bottles. Due to the light sensitivity of nicardipine, packages can be used that reduce the amount of light which can reach the composition. For example, in some embodiments, the container may, optionally, further comprise a light barrier, such as an aluminum overpouch or a carton.

In some embodiments, the premixed pharmaceutical compositions are dispensed in intravenous bags, such as pre-mix bags and admix bags. Intravenous bags are well known in the art and commercially available. Examples of intravenous bags include, but are not limited to: GALAXY®, INTRA-VIA®, SOLOMIX®, STEDIM® 71, STEDIM® 100, VIA-FLEX®, EXCEL®, VISIV®, VIAFLO™, ADDEASE®, ADD-VANTAGE®, DUPLEX™, FIRST CHOICE™, PROPYFLEX™ and BFS™.

In some embodiments, the components of the bag that come into contact with the pharmaceutical compositions should not contain polar polymers, such as polyvinyl chloride (PVC) and ethylene vinyl acetate (EVA). Examples of bags that do not contain polar polymers and thus, are suitable for use in these embodiments, include, but are not limited to, GALAXY®, EXCEL®, VISIV®, and VIAFLO™.

Procedures for filling pharmaceutical compositions in pharmaceutically acceptable containers, and their subsequent processing are known in the art. These procedures can be used to produce sterile pharmaceutical drug products often required for health care. See, e.g., Center for Drug Evaluation and Research (CDER) and Center for Veterinary Medicine (CVM), "Guidance for Industry for the Submission Documentation for Sterilization Process Validation in Applications for Human and Veterinary Drug Products", (November 1994). Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

In some embodiments, sterile pharmaceutical compositions can be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the compositions can be sterile filled into a container to avoid the heat stress of terminal sterilization.

In some embodiments, the compositions are terminally sterilized using moist heat. Terminal sterilization can be used to destroy all viable microorganisms within the final, sealed container containing the pharmaceutical composition. An autoclave is typically used to accomplish terminal heat-sterilization of drug products in their final packaging. Typical autoclave cycles in the pharmaceutical industry to achieve terminal sterilization of the final product are 121° C. for at least 10 minutes.

The pharmaceutical compositions described herein can be used for prevention or treatment of acute elevations of blood pressure in a human patient in need thereof. In some embodiments, the patients being treated may be volume-restricted due to a co-existing medical condition and thus can benefit from the administration of higher concentration and lower fluid volume of nicardipine. Examples of medical conditions in which it would be advantageous to administer low volume formulations include, renal failure, ascites, cerebral edema, congestive heart failure, liver failure, or a CNS injury. Dosages can be individualized depending upon the severity of hypertension and the response of the individual patient during dosing. Typically, the dosage is administered as a continuous infusion of a pre-mixed product. In some embodiments, the patient has an elevated blood pressure with a systolic equal to or greater than 150 mm Hg. In other embodiments, the subject has an elevated blood pressure with a diastolic value greater than or equal to 90 mm Hg.

In some embodiments, the pharmaceutical compositions can be used to prevent acute elevations of blood pressure associated with various medical procedures. Examples of medical procedures associated with acute elevations of blood pressure include, but are not limited to, electroconvulsive therapy (see, e.g., Avramov, et al., 1998, J. Clinical Anesthesia, 10:394-400), carotid endarterectomy (see, e.g., Dorman, et al., 2001, J. Clinical Anesthesia, 13:16-19, tracheal intubation (Song, et al., 2001, Anesth Analg., 85:1247-51) and skin incision (Song, et al., 2001, Anesth Analg., 85:1247-51).

In some embodiments, the pharmaceutical compositions can be used to treat acute elevations in blood pressure due to certain cardiovascular and cerebrovascular conditions. Examples of cardiovascular conditions that are associated with acute elevations of blood pressure include, but are not limited to, essential hypertension, angina, acute ischemia, systemic arterial hypertension, congestive heart failure, coronary artery disease, myocardial infarction, cardiac arrhythmias, cardiomyopathies and arteriosclerosis. Examples of cerebrovascular conditions are associated with acute elevations of blood pressure include, but are not limited to pulmonary hypertension, cerebral insufficiency and migraine headache.

In some embodiments, the pharmaceutical compositions can be used to treat other conditions that cause hypertension including, but not limited to, renal disorders (e.g., renal parenchymal disorders or renal vascular disease), coarctation of the aorta, pheochromocytoma, hyperthyroidism, metabolic syndrome, solid organ transplant and drug-related hypertension.

In some embodiments, the pharmaceutical compositions can be used to induce hypotension during surgical procedures including, but not limited to cardiothoracic surgery, spinal surgeries and head and neck surgeries.

6. ALTERNATIVE ASPECTS

In an alternative aspect, the present invention relates to pre-mixed, ready-to-use, injectable pharmaceutical compositions comprising a cardiac medication or a pharmaceutically acceptable salt thereof, and at least one of a co-solvent and a complexing agent, and a buffering agent. The composition may further comprise a tonicity agent. The compositions are preferably isotonic. The pH of the compositions is preferably between 3 and 7. The compositions are preferably packaged in a pharmaceutically acceptable container, such as an intravenous bag, syringe or vial. Preferably, the compositions are used for the treatment of cardiovascular and cerebrovascular conditions. The present invention also relates to methods for preparing such compositions. In this other aspect, the term "pre-mixed", as used herein, means a pharmaceutical composition that is already mixed from the point of manufacture and does not require dilution or further processing before administration. The term "pre-mixed" may also mean a pharmaceutical composition wherein the liquid solution and the active pharmaceutical ingredient are separated from the point of manufacture and in storage, such as when the solution is stored in an intravenous bag and the active pharmaceutical ingredient is lyophilized and stored in a vial that is connected to the bag, but not in fluid contact with the solution until just before administration to a patient. Preferably, the pharmaceutical compositions are aqueous solutions that are administered by injection. Alternatively, the pharmaceutical compositions may be lyophilized and then reconstituted in isotonic saline, for example, before intravenous administration.

In this alternative aspect, the pharmaceutical compositions of the present invention comprise a cardiac medication or a pharmaceutically acceptable salt thereof. Examples of classes of cardiac medications include beta-blockers, calcium channel antagonists, angiotensin converting enzyme inhibitors, diuretics, vasodilators, nitrates, anti-platelet medications and anti-coagulants. Preferably, the cardiac medication is a calcium channel antagonist or a pharmaceutically acceptable salt thereof. More preferably, the cardiac medication is a dihydropyridine derivative or a pharmaceutically acceptable salt thereof. Most preferably, the cardiac medication is nicardipine or a pharmaceutically acceptable salt thereof. Examples of pharmaceutically acceptable salts of nicardipine are hydrochlorides, sulfates, phosphates, acetates, fumarates, maleates and tartarates. The preferred pharmaceutically acceptable salt of nicardipine is nicardipine hydrochloride. The pharmaceutical compositions may comprise 0.05-1.5 mg/ml of nicardipine or a pharmaceutically acceptable salt thereof. Preferably, the pharmaceutical compositions comprise 0.15-0.35 mg/ml of nicardipine or a pharmaceutically acceptable salt thereof. More preferably, the compositions comprise 0.2-0.3 mg/ml of nicardipine or pharmaceutically acceptable salt thereof. Nicardipine and its pharmaceutically acceptable salts, their preparation, and their use are known in the art. For example, they are disclosed in, among other references, U.S. Pat. No. 3,985,758, which is incorporated herein by reference in its entirety.

In some embodiments, the pharmaceutical compositions comprise 0.1-15 mg/ml nicardipine or a pharmaceutically acceptable salt thereof. For example, suitable concentrations of nicardipine or a pharmaceutically acceptable salt thereof, include, but are not limited to: 0.1-15 mg/ml, 0.1-10 mg/ml, 0.1-5 mg/ml, 0.1-3.0 mg/ml, 0.1-2.0 mg/ml, 0.1-1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml or 0.1 mg/ml.

In this alternative aspect, the pharmaceutical compositions can be used to treat cardiac conditions. Preferably, the compositions can be used to treat conditions that are alleviated by the administration of calcium channel antagonists, such as cardiovascular and cerebrovascular conditions. Cardiovascular conditions that can be treated with the pharmaceutical compositions of the present invention include angina, ischemia, systemic arterial hypertension, congestive heart failure, coronary artery disease, myocardial infarction, cardiac arrhythmias, cardiomyopathies and arteriosclerosis. Cerebrovascular conditions that can be treated with the pharmaceutical compositions of the present invention include pulmonary hypertension, cerebral insufficiency and migraine. Preferably, the compositions are used to treat hypertension.

In this alternative aspect, the pharmaceutical compositions of the present invention also comprise at least one of a cosolvent and a complexing agent. Therefore, the compositions may comprise a cosolvent, a complexing agent, multiple cosolvents, multiple complexing agents, a cosolvent and a complexing agent, a cosolvent and multiple complexing agents, a complexing agent and multiple cosolvents, or multiple cosolvents and multiple complexing agents.

In this alternative aspect, Nicardipine and its pharmaceutically acceptable salts are only slightly soluble in water. Cosolvents and complexing agents help solubilize nicardipine in the aqueous solution of the pharmaceutical composition. Cosolvents and complexing agents are especially beneficial when a high concentration of nicardipine is present, such as in the compositions of the present invention. An advantage of the compositions of the present invention is that they have a high concentration of nicardipine, which allows the composition to be administered using a lower volume of intravenous fluid. Such compositions can be a treatment option for a greater number of patients, especially volume restricted patients.

In this alternative aspect, patients and medical conditions that may benefit from a higher concentration and lower fluid volume of nicardipine include, but are not limited to, the following: acute congestive cardiac failure; pediatrics; hypertensive crises in elderly patients where fluid overload is a major concern; all acute stroke areas including AIS, ICH and SAH to control blood pressure; controlled hypotension during surgical procedures including cardiothoracic surgery (CABO, coarctation of the aorta, etc.), spinal surgeries, and head and neck surgeries; and neurosurgery for the control of breakthrough hypertension post carotid endarterectomy, traumatic brain injury and potential treatment of hypertension and vasospasm.

In this alternative aspect, in addition to enhancing solubility, cosolvents and complexing agents enhance the stability of the pharmaceutical compositions. Furthermore, changes may be made to the concentration of cosolvents and complexing agents in the pharmaceutical compositions in order to adjust the tonicity of the pharmaceutical compositions. Pharmaceutically acceptable cosolvents are known in the art and are commercially available. Typical cosolvents include polyethylene glycol (PEG), propylene glycol (PG), ethanol and sorbitol. Preferably, the cosolvent concentration is 0.1-10% weight/volume percent, which will depend on the pH of the composition. More preferably, the cosolvent concentration is 0.1-5%. Most preferably, the cosolvent concentration is 0.1-2%. Preferred cosolvents for the pharmaceutical compositions are propylene glycol and sorbitol. Preferably, the concentration of propylene glycol is 0.1-2%. More preferably, the concentration of propylene glycol is 0.1-1%. Most preferably, the concentration of propylene glycol is 0.3%. A preferred concentration of sorbitol is 0.1-2%. An even more preferred concentration of sorbitol is 0.1-1%. A most preferred concentration of sorbitol is 0.5%.

In this alternative aspect, pharmaceutically acceptable complexing agents are known in the art and commercially available. Typical complexing agents include cyclodextrins, such as natural cycodextrins and chemically modified cyclodextrins. Preferably, the complexing agent is a beta cyclodextrin. Preferred complexing agents for the pharmaceutical compositions are 2-hydroxypropyl-j3-cyclodextrin (2HPBCD) and sulfobutylether-j3-cyclodextrin (SBEBCD). Preferably, the complexing agent concentration is 0.1-25% weight/volume percent. More preferably, the complexing agent concentration is 0.1-10%. Most preferably, the complexing agent concentration is 0.1-5%. Preferably, the concentration of 2HPBCD is 15-25%. More preferably, the concentration of 2HPBCD is 20-25%. The preferred concentration of SBEBCD is 0.1-10%. An even more preferred concentration of SBEBCD is 0.1-5%. The most preferred concentration of SBEBCD is 0.75 to 1%.

In addition, the pharmaceutical compositions in this alternative aspect can comprise a buffering agent. However, the compositions may comprise multiple buffering agents. The pharmaceutical compositions of the present invention are preferably close to physiological pH in order to minimize the incidence of phlebitis upon administration. However, the pH of the pharmaceutical composition also affects the solubility and stability of nicardipine in the composition. Generally, as the pH of the pharmaceutical composition increases, the aqueous solubility of nicardipine decreases. As a result, it is difficult to solubilize nicardipine close to physiological pH. In addition, the composition should have sufficient buffering capacity such that the solution does not precipitate upon dilution with blood when administered.

In this alternative aspect, typical buffering agents include acetate, glutamate, citrate, tartrate, benzoate, lactate, histidine or other amino acids, gluconate, phosphate and succinate. The preferred buffering agents are acetate and succinate. A preferred buffering agent concentration is 1-100 mM. A more preferred buffering agent concentration is 1-50 mM. An even more preferred buffering agent concentration is 25-35 mM.

In this alternative aspect, preferably, the pharmaceutical compositions of the present invention are isotonic, i.e., in the range of 270-328 mOsm/kg. However, the compositions may have a tonicity in the range of 250-350 mOsm/kg. Therefore, the compositions may be either slightly hypotonic, 250-269 mOsm/kg, or slightly hypertonic, 329-350 mOsm/kg. Preferably, the tonicity of the pharmaceutical compositions is rendered isotonic by adjusting the concentration of any one or more of cosolvent, complexing agent and buffering agent in the solution.

In this alternative aspect, the pharmaceutical compositions of the present invention may further comprise a tonicity agent. However, the compositions may further comprise multiple tonicity agents. Tonicity agents are well known in the art and commercially available. Typical tonicity agents include sodium chloride and dextrose. A preferred tonicity agent concentration is 1-200 mM. A more preferred tonicity agent concentration is 75-125 mM. An even more preferred tonicity agent concentration is 90-110 mM.

The pharmaceutical compositions of the present invention are preferably packaged in pharmaceutically acceptable containers in this alternative aspect. Pharmaceutically acceptable containers include intravenous bags, bottles, vials, and syringes. Preferred containers include intravenous bags and syringes, which are preferably polymer-based, and vials and intravenous bottles, which are preferably made of glass. It is also preferred that the components of the container that come into contact with the pharmaceutical composition do not contain polyvinylchloride (PVC). The most preferred container is an intravenous bag that does not have any PVC containing components 1n contact with the pharmaceutical composition. It is also desirable to protect the pharmaceutical compositions from light. Therefore, the container may, optionally, further comprise a light barrier. A preferred light barrier is an aluminum overpouch.

This alternative aspect also provides methods as described above for preparing the pharmaceutical compositions which are sterile.

7. EXAMPLES

Examples 1 through 6 are intended to be illustrative and not limiting as to the general disclosure. Examples 7 through 12 disclose specific embodiments of the pharmaceutical compositions that are principally illustrative of the alternative aspects described herein.

Examples 1 Through 6

Example 1: Effect of Various Diluents on Stability of Concentrated CARDENE® I.V.

Stability results for the concentrated ampul product diluted to 0.1 mg/ml with various commonly used intravenous infusion fluids in an IV bag are shown in FIG. 1. pH after mixing was measured and is reported on the X-axis.

Product stability was measured by monitoring the % drug remaining after duration of 24 hours by RP-HPLC and is shown on the Y-axis.

As shown in FIG. 1, the instability of nicardipine hydrochloride is related to the increases, for example, a very pronounced drug loss is obtained when the pH is above 4.5. Based on these findings, the product insert for the marketed ampul product requires product dilution be carried out using specific infusion fluids. Furthermore, the diluted product must be used within 24 hours.

Example 2: Effect of pH on Stability

Stability results for a 0.1 mg/mL nicardipine HC1, 0.1 mM citric acid, and 5% dextrose formulation dispensed in a GALAXY® bag are shown in FIGS. 2A and 2B. Stability results for a 0.1 mg/mL nicardipine HC1, 0.1 mM citric acid, 0.9% saline formulation dispensed in a GALAXY® bag are shown in FIGS. 3A and 3B. Stability assessments are done by measuring the % drug remaining and the total impurity formation as a function of time using RP-HPLC.

Stability testing was done at an accelerated temperature of 40° C. Based on published literature, activation energies for drug decompositions usually fall in the range of 12 to 24 Kcal/mol, with typical value of 19-20 Kcal/mol. Under these conditions (assumption Ea=19.4 Kcal/mol) 15 weeks storage at 40° C. corresponds to a product with approximately 18 months expiration at 25° C. (see, e.g., Connors, K. A., et al., Chemical Stability of Pharmaceuticals, A Handbook for Pharmacists, John Wiley & Sons, 2d ed. 1986).

As shown in FIGS. 2A and 3A, loss in product potency (drop in % drug remaining) due to degradation and adsorption on to the bag surface increased as the formulation pH was increased. For example, after 6 months storage at 40° C. for the dextrose formulations, a clear trend indicating increased drug loss for formulations at pH 4.4 and 4.7 can be observed. At pH 3.3, the drop in % drug remaining is attributed to an increase in total impurities (FIGS. 2B and 3B), rather than drug loss due to adsorption. In addition to the observed drug loss, the formation of nicardipine-related impurities (FIGS. 2B and 3B) was also found to be strongly pH dependent. In this case, however, the reverse trend was observed; as the pH was decreased, the total impurities increased.

The results from this study indicate that the formulation pH has a significant effect on stability of a ready-to-use diluted product. The findings of this study indicate that the optimal formulation pH range is between about 3.6 to about 4.7. However, depending on the degree of acceptable drug degradation and/or total impurity formation, other pH ranges can be chosen.

Example 3: Effect of Nicardipine Concentration on Impurity Formation

The effect of nicardipine concentration on impurity formation in ready to use premixed compositions comprising 0.1 mg/mL and 0.2 mg/ml non-sorbitol formulations with dextrose over 6 months at 40° C. is shown in FIG. 4A. The effect of nicardipine concentration on impurity formation in ready to use premixed compositions comprising 0.1 mg/ml and 0.2 mg/mL non-sorbitol formulations with saline over 3 months at 40° C. is shown in FIG. 4B. The formulations are dispensed in GALAXY® bags. Stability assessments are done as described in Example 2.

As shown in FIGS. 4A and 4B, in addition to pH, product concentration is another factor that impacts product stability, in particular the formation of nicardipine-related impurities. The concentration dependence observed with respect to total impurity formation is minimized as the formulation pH is increased. For example, in FIGS. 4A and B, the effect of concentration is significant at pH 3.3 and is minimized as the pH approaches 4.7.

These results indicate that impurity formation is greater for the 0.1 mg/ml formulations as compared to the 0.2 mg/ml formulations for both the dextrose and saline formulations. Simultaneous optimization of the drug concentration along with the viable formulation pH range is important in the development of ready-to-use premixed drug formulations.

Example 4: Stability Comparison of Sorbitol and Non-Sorbitol Formulations

A stability comparison of sorbitol and non-sorbitol formulations was conducted under accelerated conditions (4 weeks at 40° C.) using a 0.1 mg/mL nicardipine HCI, 1.92 mg/mL sorbitol, 48 mg/mL dextrose, 0.0192 mg/mL citric acid, pH 4.2 and a 0.1 mg/mL nicardipine HCI, 50 mg/mL dextrose, 0.0192 mg/mL citric acid, pH 4.0. Both formulations were dispensed in GALAXY® bags. Stability assessments were done by measuring the % drug remaining and total impurity formation as a function of time using RP-HPLC. The results are shown in Tables 2 and 3.

TABLE 2

Dextrose Formulation without Sorbitol

| Time | % Drug Remaining | % Total Impurities |
|---|---|---|
| 0 | 100.0 | 0.08 |
| 4 | 98.1 | 0.17 |

TABLE 3

Dextrose Formulation with Sorbitol

| Time | % Drug Remaining | % Total Impurities |
|---|---|---|
| 0 | 100.0 | NMT[1] 0.05 |
| 4 | 96.4 | 0.13 |

[1]NMT refers to no more than.

As shown in Tables 2 and 3, minimal differences between the two formulations were observed in the measured parameters. Based on these results, as well as the results shown in Examples 1 and 2, the presence or absence of sorbitol is not predicted to alter the impact of formulation pH and drug concentration on the stability of the premixed pharmaceutical compositions comprising nicardipine HC1 and dextrose or sodium chloride.

Example 5: The Effect of Plastic Film Composition on Stability

The effect of plastic film composition on the stability of ready to use premixed compositions comprising 0.2 mg/mL nicardipine HC1, 0.2 mM citrate, 5% dextrose, pH 4.0-4.2 for "incompatible" bags and "compatible" bags is shown in FIGS. 5A and 5B respectively. "Incompatible" bags contain polar polymers, such as polyvinyl chloride (PVC) and ethylene vinyl acetate (EVA). "Compatible" bags do not contain polar polymers.

Stability evaluations were done for the 0.2 mg/mL non-sorbitol dextrose formulation in various commercially available IV infusion bag systems. EXCEL®, VIAFLEX®, VIAFLO™ INTRAVIA®, and VISIV® bags were rinsed in water and covered with aluminum foil over pouches. The bags were filled with the above formulation and autoclaved at 105° C. for 21 minutes. STEDIM® 71 and GALAXY® bags were aseptically filled with the above formulation. Stability assessments were done by measuring the % drug remaining and total impurity formation (data not shown) as a function of time using RP-HPLC for samples incubated for up to 24 weeks at 40° C. The % drug remaining was calculated relative to the concentration measured post-mixing in tank.

As shown in FIG. 5A, various commercially available IV bags were not compatible with nicardipine HCl. Significant loss in product potency was observed upon storage primarily due to product adsorption in bags that contained the polymer PVC (e.g., VIAFLEX® and INTRAVIA®). Nicardipine was also incompatible with bags containing the polymer ethylene-vinyl acetate (EVA) in the contact layer (e.g., STEDIM®71). PVC and EVA are examples are of polar plastic materials that are incompatible with nicardipine HC1. Because nicardipine HCl is a weak base with a pKa of ~7.2, it is increasingly hydrophobic as the formulation pH increases, and therefore, compatibility with polymeric contact surfaces is dependent on surface charge-related properties.

As shown in FIG. 5B, minimal drop in product potency was observed with commercial bags comprising copolyester (e.g., EXCEL®), polyethylene (e.g., GALAXY®), and polyolefin blends (e.g., VISIV® and VIAFLO™).

Example 6: Effect of CAPTISOL® on Product Stability

The effect of CAPTISOL® on the stability of ready to use premixed compositions comprising 0.3 mg/ml Nicardipine, 30 mM NaAcetate, 1.8% Captisol, 112 mM NaCl, pH 4.5 or 0.3 mg/ml Nicardipine, 30 mM NaAcetate, 1.8% Captisol, 3.7% Dextrose, pH 4.5 dispensed in 100 ml GALAXY® bags was monitored for 12 weeks at 5, 25 and 40° C. in (see, e.g., Table 4). Because the drug was stable at 5° C., the data is not shown. In addition, the formulations were monitored at 45° C. in 2 mL glass vials (see, e.g., Table 5). All formulations were filled aseptically into the vials and bags by filtering the solution through a 0.22 µm filter.

TABLE 4

% Drug Remaining at 25° C. and 40° C. in GALAXY ® Bag

| Time (weeks) | % Drug remaining at 25° C. | | % Drug remaining at 40° C. | |
| --- | --- | --- | --- | --- |
| | NaCl Formulation | Dextrose Formulation | NaCl Formulation | Dextrose Formulation |
| 0 | 100.00 | 100.00 | 100.00 | 100.00 |
| 1 | 96.57 | 99.86 | 97.15 | 98.86 |
| 2 | 98.09 | 100.80 | 97.07 | 100.40 |
| 4 | 99.45 | 104.01 | 98.46 | 102.56 |
| 12 | 97.23 | 101.18 | 95.36 | 99.00 |

TABLE 5

% Drug Remaining at 45° C. in Glass Vials
% Drug Remaining

| Time (weeks) | NaCl Formulation | Dextrose Formulation |
| --- | --- | --- |
| 0 | 100.00 | 100.00 |
| 2 | 107.69 | 105.78 |
| 4 | 105.18 | 105.22 |
| 14 | 102.22 | 102.80 |

Pharmaceutical compositions comprising CAPITSOL® exhibited minimal drug loss and impurity formation (data not shown) as a function of time and temperature. Based on the accelerated stability data at 40° and 45° C., formulations comprising CAPTISOL®, dextrose or NAC1 should be stable at room temperature for at least 12 months.

Examples 7 Through 12

Examples 7-12 illustrate experiments performed using specific embodiments. The experiments in Example 7-12 were performed at 45° C. in order to simulate stressed conditions that cause sufficient product degradation in a relatively short period of time. Stability comparisons were done against the control formulation (CF) and/or the commercial product formulation (CPF) in order to assess relative differences in their degradation profiles. The CPF is a marketed drug product and, therefore, degradation behavior of the molecule is well understood as a function of temperature and time. Stability data are available for the marketed product up to 36 months at room temperature, 22-27° C., and 40° C.

The rationale used in this preliminary screening evaluation is that if the degradation kinetics of the evaluated formulation prototypes were comparable to the CPF at stressed temperatures, drug product stability would likely be comparable or better at room temperature. The current prototype formulation is stable for at least 18 months at 25° C., and therefore it is projected that the evaluated formulation prototypes can have comparable or better stability.

Example 7: Formulation Preparation and Analysis

Appropriate buffers, such as acetate or succinate, containing the desired cosolvents, such as sorbitol or propylene glycol, and/or complexing agents, such as SBEBCD or 2HPBCD, were prepared. Appropriate tonicity agents, such as sodium chloride, were prepared and added to some of the pharmaceutical compositions. Based upon the final formulation volume and the target drug concentration, usually 0.2-0.3 mg/mL, nicardipine was weighed into an appropriate glass container and prepared buffer was added to dissolve the drug. Tonicity agent, if any, was then added. The solution was then sonicated for up to 45 minutes to facilitate drug dissolution. Following drug dissolution, the solution was filtered through a 0.45 µm syringe filter (Acrodisc LC 13 mm Syringe filter, PVDF Membrane from Life Sciences, PN 4452T). When filtering, the first few drops were discarded and the remaining solution was collected into another glass container. The prepared formulations were subsequently dispensed into either vials or intravenous bags.

The following isotonic pharmaceutical compositions were made according to the above protocol:

Pharmaceutical Composition 1 (PC 1): 0.2-0.3 mg/ml nicardipine hydrochloride, 3.7% sorbitol, and 50 mM Na-acetate, wherein the pH of the composition is 5.0.

Pharmaceutical Composition 2 (PC 2): 0.2-0.3 mg/ml nicardipine hydrochloride, 1.7% propylene glycol, and 50 mM Na-acetate, wherein the pH of the composition is 5.0.

Pharmaceutical Composition 3 (PC 3): 0.2-0.3 mg/ml nicardipine hydrochloride, 2.8% sorbitol, and 50 mM Na-succinate, wherein the pH of the composition is 5.5.

Pharmaceutical Composition 4 (PC 4): 0.2-0.3 mg/ml nicardipine hydrochloride, 1.1% propylene glycol, and 50 mM Na-succinate, wherein the pH of the composition is 5.5.

Pharmaceutical Composition 5 (PC 5): 0.2-0.3 mg/ml nicardipine hydrochloride, 4.1% sorbitol, and 50 mM Na-acetate, wherein the pH of the composition is 3.5.

Pharmaceutical Composition 6 (PC 6): 0.2-0.3 mg/ml nicardipine hydrochloride, 1.9% propylene glycol, and 50 mM Na-acetate, wherein the pH of the composition is 3.5.

Pharmaceutical Composition 7 (PC 7): 0.2-0.3 mg/ml nicardipine hydrochloride, 4.1% sorbitol, and 50 mM Na-acetate, wherein the pH of the composition is 4.5.

Pharmaceutical Composition 8 (PC 8): 0.2-0.3 mg/ml nicardipine hydrochloride, 1.8% propylene glycol, and 50 mM Na-acetate, wherein the pH of the composition is 4.5.

Pharmaceutical Composition 9 (PC 9): 0.2-0.3 mg/ml nicardipine hydrochloride, 6.5% sulfobutylether-β-cyclodextrin, and 50 mM Na-succinate, wherein the pH of the composition is 5.5.

Pharmaceutical Composition 10 (PC 10): 0.2-0.3 mg/ml nicardipine hydrochloride, 6.5% sulfobutylether-β-cyclodextrin, and 50 mM Na-succinate, wherein the pH of the composition is 6.0.

Pharmaceutical Composition 11 (PC 11): 0.2-0.3 mg/ml nicardipine hydrochloride, 8.5% sulfobutylether-β-cyclodextrin, and 50 mM Na-succinate, wherein the pH of the composition is 5.5.

Pharmaceutical Composition 12 (PC 12): 0.2-0.3 mg/ml nicardipine hydrochloride, 8.5% sulfobutylether-β-cyclodextrin, and 50 mM Na-succinate, wherein the pH of the composition is 6.0.

Pharmaceutical Composition 13 (PC 13): 0.2-0.3 mg/ml nicardipine hydrochloride, 8.5% sulfobutylether-β-cyclodextrin, and 50 mM Na-acetate, wherein the pH of the composition is 5.0.

Pharmaceutical Composition 14 (PC 14): 0.2-0.3 mg/ml nicardipine hydrochloride, 8.5% sulfobutylether-β-cyclodextrin, and 50 mM Na-citrate, wherein the pH of the composition is 5.5.

Pharmaceutical Composition 15 (PC 15): 0.2-0.3 mg/ml nicardipine hydrochloride, 22.5% 2-hydroxypropyl-β-cyclodextrin, and 50 mM Na-acetate, wherein the pH of the composition is 5.0.

Pharmaceutical Composition 16 (PC 16): 0.2-0.3 mg/ml nicardipine hydrochloride, 22.5% 2-hydroxypropyl-β-cyclodextrin, and 50 mM Na-succinate, wherein the pH of the composition is 5.5.

Pharmaceutical Composition 17 (PC 17): 0.2-0.3 mg/ml nicardipine hydrochloride, 17.5% 2-hydroxypropyl-β-cyclodextrin, and 50 mM Na-acetate, wherein the pH of the composition is 5.0.

Pharmaceutical Composition 18 (PC 18): 0.2-0.3 mg/ml nicardipine hydrochloride, 17.5% 2-hydroxypropyl-βcyclodextrin, and 50 mM Na-succinate, wherein the pH of the composition is 5.5.

Commercial Product (Ampul) Formulation (CPF): 2.5 mg/ml nicardipine Control Formulation (CF): 0.3 mg/ml nicardipine hydrochloride, 2.5 mM citrate, and 5% sorbitol, wherein the pH of the composition is 3.5.

Pharmaceutical Composition 19 (PC 19): 0.3 mg/ml nicardipine hydrochloride, 50 mM sodium acetate, 50 mM sodium citrate, and 50 mM disodium succinate, wherein the pH of the composition is 3.5.

Pharmaceutical Composition 20 (PC 20): 0.3 mg/ml nicardipine hydrochloride, 50 mM sodium acetate, 50 mM sodium citrate, and 50 mM disodium succinate, wherein the pH of the composition is 4.5.

Pharmaceutical Composition 21 (PC 21): 0.3 mg/ml nicardipine hydrochloride, 50 mM sodium acetate, 50 mM sodium citrate, and 50 mM disodium succinate, wherein the pH of the composition is 5.0.

Pharmaceutical Composition 22 (PC 22): 0.3 mg/ml nicardipine hydrochloride, 50 mM sodium acetate, 50 mM sodium citrate, and 25 mM disodium succinate, wherein the pH of the composition is 5.5.

Pharmaceutical Composition 23 (PC 23): 0.3 mg/ml nicardipine hydrochloride, 4.1% sorbitol, and 50 mM sodium acetate, wherein the pH of the composition is 3.5.

Pharmaceutical Composition 24 (PC 24): 0.3 mg/ml nicardipine hydrochloride, 4.1% sorbitol, and 50 mM sodium acetate, wherein the pH of the composition is 4.5.

Pharmaceutical Composition 25 (PC 25): 0.3 mg/ml nicardipine hydrochloride, 3.7% sorbitol, and 50 mM sodium acetate, wherein the pH of the composition is 5.0.

Pharmaceutical Composition 26 (PC 26): 0.3 mg/ml nicardipine hydrochloride, 2.8% sorbitol, and 50 mM sodium acetate, wherein the pH of the composition is 5.5.

Pharmaceutical Composition 27 (PC 27): 0.3 mg/ml nicardipine hydrochloride, 1.9% propylene glycol, and 50 mM sodium acetate, wherein the pH of the composition is 3.5.

Pharmaceutical Composition 28 (PC 28): 0.3 mg/ml nicardipine hydrochloride, 1.8% propylene glycol, and 50 mM sodium acetate, wherein the pH of the composition is 4.5.

Pharmaceutical Composition 29 (PC 29): 0.3 mg/ml nicardipine hydrochloride, 1.7% propylene glycol, and 50 mM sodium acetate, wherein the pH of the composition is 5.0.

Pharmaceutical Composition 30 (PC 30): 0.3 mg/ml nicardipine hydrochloride, 1.1% propylene glycol, and 50 mM sodium succinate, wherein the pH of the composition is 5.5.

Pharmaceutical Composition 31 (PC 31): 0.3 mg/ml nicardipine hydrochloride, 6.5% sulfobutylether-β-cyclodextrin, and 50 mM sodium succinate, wherein the pH of the composition is 5.5.

Pharmaceutical Composition 32 (PC 32): 0.3 mg/ml nicardipine hydrochloride, 6.5% sulfobutylether-β-cyclodextrin, and 50 mM sodium succinate, wherein the pH of the composition is 6.0.

Pharmaceutical Composition 33 (PC 33): 0.3 mg/ml nicardipine hydrochloride, 22.5% 2-hydroxypropyl-β-cyclodextrin, and 50 mM sodium acetate, wherein the pH of the composition is 5.0.

Pharmaceutical Composition 34 (PC 34): 0.3 mg/ml nicardipine hydrochloride, 17% 2-hydroxypropyl-β-cyclodextrin, and 50 mM disodium succinate, wherein the pH of the composition is 5.5.

Pharmaceutical Composition 35 (PC 35): 0.3 mg/ml nicardipine hydrochloride, 0.3% propylene glycol, 0.5% sorbitol, 30 mM sodium acetate, and 90 mM NaCl, wherein the pH of the composition is 5.2.

Pharmaceutical Composition 36 (PC 36): 0.3 mg/ml nicardipine hydrochloride, 0.3% propylene glycol, 2.0% sorbitol, 30 mM sodium acetate, 45 mM NaCl, wherein the pH of the composition is 5.2.

Pharmaceutical Composition 37 (PC 37): 1.5 mg/ml nicardipine hydrochloride, 9% sulfobutylether-β-cyclodextrin, and 30 mM sodium acetate, wherein the pH of the composition is 4.5.

Pharmaceutical Composition 38 (PC 38): 1.5 mg/ml nicardipine hydrochloride, 9% sulfobutylether-β-cyclodextrin, and 30 mM sodium acetate, wherein the pH of the composition is 5.0.

Pharmaceutical Composition 39 (PC 39): 0.3 mg/ml nicardipine hydrochloride, and 30 mM sodium acetate, wherein the pH of the composition is 3.5.

Pharmaceutical Composition 40 (PC 40): 0.3 mg/ml nicardipine hydrochloride, and 30 mM sodium acetate, wherein the pH of the composition is 4.0.

Pharmaceutical Composition 41 (PC 41): 0.3 mg/ml nicardipine hydrochloride, and 30 mM sodium acetate, wherein the pH of the composition is 4.5.

Pharmaceutical Composition 42 (PC 42): 0.3 mg/ml nicardipine hydrochloride, 1.8% sulfobutylether-β-cyclodextrin, 30 mM sodium acetate, and 110 mM NaCl, wherein the pH of the composition is 5.0.

Pharmaceutical Composition 43 (PC 43): 0.3 mg/ml nicardipine hydrochloride, 1.8% sulfobutylether-β-cyclodextrin, 0.3% propylene glycol, 30 mM sodium acetate, and 85 mM NaCl, wherein the pH of the composition is 5.0.

Pharmaceutical Composition 44 (PC 44): 0.3 mg/ml nicardipine hydrochloride, 1.8% sulfobutylether-β-cyclodextrin, 30 mM sodium acetate, and 110 mM NaCl, wherein the pH of the composition is 4.5.

Pharmaceutical Composition 45 (PC 45): 0.3 mg/ml nicardipine hydrochloride, 1.8% sulfobutylether-β-cyclodextrin, 30 mM sodium acetate, and 200 mM dextrose, wherein the pH of the composition is 4.5.

Pharmaceutical Composition 46 (PC 46): 0.3 mg/ml nicardipine hydrochloride, 0.75% sulfobutylether-β-cyclodextrin, 30 mM sodium acetate, and 125 mM NaCl, wherein the pH of the composition is 4.5.

Pharmaceutical Composition 47 (PC 47): 0.3 mg/ml nicardipine hydrochloride, 1.0% sulfobutylether-β-cyclodextrin, 30 mM sodium acetate, and 125 mM NaCl, wherein the pH of the composition is 4.5.

Pharmaceutical Composition 48 (PC 48): 0.3 mg/ml nicardipine hydrochloride, 3.4% sorbitol, and 50 mM sodium succinate, wherein the pH of the composition is 5.6.

Pharmaceutical Composition 49 (PC 49): 0.3 mg/ml nicardipine hydrochloride, 1.3% propylene glycol, and 50 mM sodium acetate, wherein the pH of the composition is 5.6.

Pharmaceutical Composition 50 (PC 50): 0.3 mg/ml nicardipine hydrochloride, 1.8% sulfobutylether-β-cyclodextrin, 30 mM sodium acetate, and 110 mM NaCl, wherein the pH of the composition is 5.0.

Pharmaceutical Composition 51 (PC 51): 0.3 mg/ml nicardipine hydrochloride, 0.75% sulfobutylether-β-cyclodextrin, 30 mM sodium acetate, and 125 mM NaCl, wherein the pH of the composition is 4.5.

Pharmaceutical Composition 52 (PC 52): 0.3 mg/ml nicardipine hydrochloride, 1.0% sulfobutylether-β-cyclodextrin, 30 mM sodium acetate, and 125 mM NaCl, wherein the pH of the composition is 4.5.

Pharmaceutical Composition 53 (PC 53): 0.3 mg/ml nicardipine hydrochloride, 0.5% sorbitol, 0.3% propylene glycol, 30 mM sodium acetate, and 90 mM NaCl, wherein the pH of the composition is 5.2.

Pharmaceutical Composition 54 (PC 54): 0.3 mg/ml nicardipine hydrochloride, 1.0% sulfobutylether-β-cyclodextrin, 30 mM sodium acetate, and 125 mM NaCl, wherein the pH of the composition is 4.5.

Pharmaceutical Composition 55 (PC 55): 0.3 mg/ml nicardipine hydrochloride, 0.75% sulfobutylether-β-cyclodextrin, 30 mM sodium acetate, and 125 mM NaCl, wherein the pH of the composition is 4.5.

Pharmaceutical Composition 56 (PC 56): 0.3 mg/ml nicardipine hydrochloride, 0.5% sorbitol, 0.3% propylene glycol, 50 mM sodium acetate, and 90 mM NaCl, wherein the pH of the composition is 5.2.

The excipient concentration in the control formulation (CF) is identical to the commercial product formulation (CPF), Cardene® I.V (ampul). However, the concentration of active ingredient in the commercial and control formulations is different. In the commercial product formulation (CPF), the concentration of nicardipine hydrochloride in the ampul is 2.5 mg/mL before dilution, and 0.1 mg/ml after dilution with appropriate IV fluids before administration. The control formulation (CF), which is designed for pre-mixed ready-to-use intravenous bags such that no further dilution with intravenous fluids is required, has a nicardipine hydrochloride concentration of 0.3 mg/mL. The purpose of the control formulation was to help assess the degradation propensity of the evaluated formulations. Comparable degradation profiles at stressed conditions is indicative of comparable formulation stability.

Example 8: Vial Stability Data with Sorbitol and Propylene Glycol Formulations

The stability in vials of pharmaceutical compositions of the present invention comprising a co-solvent and a buffering agent were compared to the control formulation and the commercial product formulation. Stability was determined by comparing the drug concentration over time for the below compositions. Specifically, the below compositions were prepared according to the method in Example 7:

50 mM Na-acetate, pH 3.5, 4.1% sorbitol (PC 5),
50 mM Na-acetate, pH 4.5, 4.1% sorbitol (PC 7),
50 mM Na-acetate, pH 4.5, 1.8% propylene glycol (PC 8),
50 mM Na-acetate, pH 5.0, 3.7% sorbitol (PC 1),
50 mM Na-acetate, pH 5.0, 1.7% propylene glycol (PC 2),
Control formulation: 0.3 mg/mL, 2.5 mM citrate, 5% sorbitol, pH 3.5 (CF), and
Commercial product formulation: 2.5 mg/ml, 2.5 mM citrate, 5% sorbitol, pH 3.5 (CPF).

These stability studies were performed in 2 ml glass vials and at elevated temperature conditions, in this case 45° C. Formulation stability was monitored by measuring the drug concentration by RP-HPLC against a standard curve. The drug concentration measurements were taken at the start of the experiment, 7 days and 21 days, except for the commercial product formulation, which measurements were taken at the start of the experiment and 46 days. These measurements were then converted into a percentage in order to show the percentage of drug remaining after a period of time.

| PC# | Drug Conc. (µg/ml) t = 0 | % Drug Remaining | Drug Conc. (µg/ml) t = 7 days | % Drug Remaining | Drug Conc. (µ/ml) t = 21 days | % Drug Remaining |
|---|---|---|---|---|---|---|
| 5 | 314 | 100 | 312 | 99 | 289 | 92 |
| 6 | 302 | 100 | 305 | 101 | 282 | 93 |
| 7 | 304 | 100 | 303 | 100 | 283 | 93 |
| 8 | 304 | 100 | 304 | 100 | 282 | 93 |

-continued

| | | | | | | |
|---|---|---|---|---|---|---|
| 1 | 298 | 100 | 294 | 98 | 274 | 92 |
| 2 | 290 | 100 | 302 | 104 | 264 | 91 |
| CF | 302 | 100 | 301 | 100 | 277 | 92 |

| PC# | Drug Conc. (µg/ml) t = 0 | % Drug Remaining | Drug Conc. (µg/ml) t = 46 days | % Drug Remaining |
|---|---|---|---|---|
| CF | 2553 | 100 | 2265 | 89 |

The data show that the stability in vials, drug concentration over time, of the pharmaceutical compositions of the present invention that contain co-solvents are comparable to both the control formulation (CF) and the current product formulation (CPF). In addition, the compositions had no additional degradation products relative to the control formulation (data not shown).

Example 9: Vial Stability Data with SBEBCD Formulations

The stability in vials of pharmaceutical compositions of the present invention comprising a complexing agent and a buffering agent were compared to the control formulation and the commercial product formulation. Stability was determined by comparing the drug concentration over time for the below compositions. Specifically, the below compositions were prepared according to the method in Example 7:

50 mM Na-acetate, 8.5% SBE-beta cyclodextrin, pH 5.0 (PC 13),
50 mM Na-citrate, 8.5% SBE-beta cyclodextrin, pH 5.5 (PC 14),
50 mM Na-succinate, 8.5% SBE-beta cyclodextrin, pH 5.5 (PC 11),
50 mM Na-succinate, 8.5% SBE-beta cyclodextrin, pH 6.0 (PC 12),
Control formulation: 0.3 mg/mL, 2.5 mM citrate, 5% sorbitol, pH 3.5 (CF), and
Commercial product formulation: 2.5 mg/ml, 2.5 mM citrate, 5% sorbitol, pH 3.5 (CPF).

These stability studies were performed in 2 ml glass vials and at vials and at elevated temperature conditions, in this case 45° C. Formulation stability was monitored by measuring the drug concentration by RP-HPLC against a standard curve. The drug concentration measurements were taken at the start of the experiment, 6 days, 13 days and 30 days, except for the commercial product formulation, which measurements were taken at the start of the experiment and 46 days. These measurements were then converted into a percentage in order to show a percentage of drug remaining after a period of time.

The data from these stability studies are shown in the following Tables.

| PC# | [Drug] (µg/ml) t = 0 | % [Drug] Remaining | [Drug] (µg/ml) t = 6 d | % [Drug] Remaining | [Drug] (µg/ml) t = 13 d | % [Drug] Remaining | [Drug] (µg/ml) t = 30 d | % [Drug] Remaining |
|---|---|---|---|---|---|---|---|---|
| 13 | 381 | 100 | 387 | 101 | 413 | 108 | 390 | 102 |
| 14 | 334 | 100 | 339 | 101 | 352 | 105 | 333 | 100 |
| 11 | 364 | 100 | 378 | 104 | 396 | 109 | 364 | 100 |
| 12 | 318 | 100 | 341 | 107 | 355 | 112 | 326 | 103 |
| CF | 339 | 100 | 352 | 104 | 363 | 107 | 338 | 100 |

| PC# | Drug Conc. (µg/ml) t = 0 | % Drug Remaining | Drug Conc. (µg/ml) t = 46 days | % Drug Remaining |
|---|---|---|---|---|
| CPF | 2553 | 100 | 2265 | 89 |

The data show that the stability in vials, drug concentration over time, of the pharmaceutical compositions of the present invention that contain SBEBCD are comparable to both the control formulation (CF) and the commercial product formulation (CPF). In addition, the compositions had no additional degradation products relative to the control formulation (data not shown). It is also worth noting that the target concentration of 0.2-0.3 mg/mL could be readily attained in the presence of sulfobutlyether-β-cyclodextrin.

Example 10: Intravenous Bag Stability Data with Sorbitol and Propylene Glycol Formulations The stability in intravenous bags of pharmaceutical compositions of the present invention comprising a co-solvent and a buffering agent were compared to a control formulation. Stability was determined by comparing the drug concentration over time for the below compositions. Specifically, the below compositions were prepared according to the method in Example 7:

50 mM Na-acetate, pH 3.5. 4.1% sorbitol (PC 5), 50 mM Na-acetate, pH 3.5. 1.9% propylene glycol (PC 6), and Control formulation: 0.3 mg/mL, 2.5 mM citrate, 5% sorbitol, pH 3.5 (CF).

These stability studies were performed in 50 ml intravenous bags and at elevated temperature conditions, in this case 45° C. Formulation stability was monitored by measuring the drug concentration by RP-HPLC against a standard curve. The drug concentration measurements were taken at the start of the experiment, 7 days and 21 days. These measurements were then converted into a percentage in order to show the percentage of drug remaining after a period of time.

The data from these stability studies are shown in the Table below.

| PC# | Drug Conc. (μ/ml) t = 0 | % Drug Remaining | Drug Conc. (μ/ml) t = 7 days | % Drug Remaining | Drug Conc. (μ/ml) t = 21 days | % Drug Remaining |
|---|---|---|---|---|---|---|
| 5 | 314 | 100 | 317 | 101 | 319 | 102 |
| 6 | 302 | 100 | 311 | 103 | 297 | 98 |
| CF | 302 | 100 | 276 | 92 | 264 | 88 |

The data show that the stability in intravenous bags, drug concentration over time, of the pharmaceutical compositions of the present invention that contain co-solvents are comparable to the control formulation. In addition, the compositions had no additional degradation products relative to the control formulation (data not shown). Finally, drug adsorption on the bag surface was minimal at pH 3.5.

Example 11: Intravenous Bag Stability Data with HPCD Formulations

The stability of a pharmaceutical composition of the present invention comprising a complexing agent and a buffering agent was evaluated in both vials and intravenous bags. Stability was determined by comparing the drug concentration over time for the below composition. Specifically, the below composition was prepared according to the method in Example 7:

50 mM Na-acetate, pH 5.0, 22.5% HPCD (PC 15).

These stability studies were performed in 50 ml intravenous bags and at elevated temperature conditions, in this case 45° C. The stability evaluations were done with a 10 mL fill volume in both the upright and inverted bag configurations. These evaluations were done relative to the same formulation in a 2 mL glass vial, as a control. Formulation stability was monitored by measuring the drug concentration by RP-HPLC against a standard curve. The drug concentration measurements were taken at the start of the experiment, 1 day, 2 days, 6 days, 9 days and 16 days.

The data from these stability studies are shown in the Table below.

| | Drug Conc. (μ/ml) t = 0 | Drug Conc. (μ/ml) t = 1 day | Drug Conc. (μ/ml) t = 2 days | Drug Conc. (μ/ml) t = 6 days | Drug Conc. (μ/ml) t = 9 days | Drug Conc. (μ/ml) t = 16 days |
|---|---|---|---|---|---|---|
| Vial | 271 | 271 | 263 | 260 | 269 | 274 |
| Upright Bag | 271 | 266 | 244 | 264 | 270 | 301 |
| Inverted | 271 | 233 | 203 | 175 | 172 | 150 |

The data show that the stability, drug concentration over time, of the pharmaceutical composition of the present invention that contains complexing agent is more promising in the upright configuration of the bag. The data also show that the recovery of drug product was poorer in the inverted bag configuration.

In order to determine why the composition was more stable in upright intravenous bags compared to inverted intravenous bags, additional experiments were conducted. The drop in drug concentration was not due to any new degradation product (data not shown). We believe that the drop in drug concentration was due to drug adsorption on the bag surface. For many hydrophobic drugs, adsorption on PVC surfaces is a commonly reported concern. Therefore, it is likely that we observed significant adsorption in the inverted configuration because the drug is in contact with PVC surfaces. These results suggest the use of non-PVC bags and/or the careful evaluation of the bag size (solution volume) as feasible options to minimize drug adsorption in order to achieve adequate drug product recovery.

Example 12: Intravenous Bag Stability Data with Sorbitol Formulations

The stability of a pharmaceutical composition of the present invention comprising a cosolvent and a buffering agent was evaluated in both vials and intravenous bags. Stability was determined by comparing the drug concentration over time for the below composition. Specifically, the below composition was prepared according to the method in Example 7:

50 mM Na-acetate, pH 5.0, 3.7% sorbitol (PC 1).

These stability studies were performed in 50 ml intravenous bags and at elevated temperature conditions, in this case 45° C. The stability evaluations were done with both 10 and 50 mL fill volumes in both the upright and inverted bag configurations. These evaluations were done relative to the same formulation in a 2 mL glass vial, as a control. Formulation stability was monitored by measuring the drug concentration by RP-HPLC against a standard curve. The drug concentration measurements were taken at the start of the experiment, 1 day, 2 days, 5 days, 9 days and 16 days.

The data from these stability studies are shown in the below Table.

| | Drug Conc. (μ/ml) t = 0 | Drug Conc. (μ/ml) t = 1 day | Drug Conc. (μ/ml) t = 2 days | Drug Conc. (μ/ml) t = 6 days | Drug Conc. (μ/ml) t = 9 days | Drug Conc. (μ/ml) t = 16 days |
|---|---|---|---|---|---|---|
| Vial | 100 | 102 | 100 | 110 | 104 | 106 |
| Upright Bag 10 ml | 100 | 93 | 89 | 98 | 85 | 87 |
| Upright Bag 50 ml | 100 | 98 | 96 | 114 | 97 | 98 |
| Inverted Bag 10 ml | 100 | 46 | 43 | 38 | 21 | 13 |
| Inverted Bag 50 ml | 100 | 89 | 87 | 102 | 86 | 85 |

The data show that the stability, drug concentration over time, of the pharmaceutical composition of the present invention that contains cosolvent is more promising in the upright configuration of the bag. The data also show that the recovery of drug product was poorer in the inverted bag configuration.

In order to determine why the composition was more stable in upright intravenous bags compared to inverted intravenous bags, additional experiments were conducted. The drop in drug concentration was not due to any new degradation product (data not shown). We believe that the drop in drug concentration was due to drug adsorption on the bag surface. For many hydrophobic drugs, adsorption on PVC surfaces is a commonly reported concern. Therefore, it is likely that we observed significant adsorption in the inverted configuration because the drug is in contact with PVC surfaces. This belief is fill configuration relative to the 50 mL fill configuration, although this poorer recovery may be partly due to the fact that the 10 mL fill configuration has a higher surface area to volume ratio, which adversely impacts drug adsorption and recovery. In conclusion, these results suggest the use of non-PVC bags and/or the careful evaluation of the bag size (solution volume) as feasible options to minimize drug adsorption in order to achieve adequate drug product recovery.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A pharmaceutical composition for parenteral administration comprising a pre-mixed aqueous solution comprising:
   from about 0.1 to 0.4 mg/mL nicardipine or a pharmaceutically acceptable salt thereof; and
   a tonicity agent;
   the aqueous solution contained in a pharmaceutically acceptable container such that the solution is in contact with non-polar polymers;
   wherein the composition requires no dilution before administration and is buffered to a pH from about 3.6 to about 4.4, the aqueous solution when stored in the container for at least three months at room temperature exhibiting (i) less than a 10% decrease in the concentration of nicardipine or pharmaceutically acceptable salt thereof and (ii) a total impurity formation of less than about 3%.

2. The pharmaceutical composition for parenteral administration of claim 1, the aqueous solution when stored in the container for at least one year at room temperature exhibiting (i) less than a 10% decrease in the concentration of nicardipine or pharmaceutically acceptable salt thereof and (ii) a total impurity formation of less than about 3%.

3. The composition of claim 1, further comprising from about 1 mg/mL to about 4 mg/mL sorbitol.

4. The composition of claim 1, wherein the non-polar polymers comprise copolyester, polyethylene or polyolefin.

5. The composition of claim 1, comprising from about 0.1 to 0.2 mg/mL nicardipine or a pharmaceutically acceptable salt thereof.

6. The composition of claim 1, further comprising from about 0 mg/mL to about 4 mg/mL sorbitol.

7. The composition of claim 1, wherein the tonicity agent comprises dextrose.

8. The composition of claim 7, comprising about 4.5% to about 5% w/v dextrose based on the composition.

9. The composition of claim 1, wherein the tonicity agent comprises sodium chloride.

10. The composition of claim 9, comprising about 0.8% to about 0.9% w/v sodium chloride based on the composition.

* * * * *